US009150803B2

(12) United States Patent
Jovanovic et al.

(10) Patent No.: US 9,150,803 B2
(45) Date of Patent: Oct. 6, 2015

(54) SYSTEMS AND METHODS FOR BIOMASS GRINDING AND FEEDING

(75) Inventors: Zoran Jovanovic, Louisville, CO (US); Bryan Schramm, Broomfield, CO (US); Christopher Perkins, Boulder, CO (US); Courtland Hilton, Broomfield, CO (US); Wayne Simmons, Dublin, OH (US)

(73) Assignee: Sundrop Fuels, Inc., Longmont, CO (US)

(*) Notice: Subject to any disclaimer, the term of this patent is extended or adjusted under 35 U.S.C. 154(b) by 1181 days.

(21) Appl. No.: 12/796,222

(22) Filed: Jun. 8, 2010

(65) Prior Publication Data

US 2010/0242353 A1     Sep. 30, 2010

Related U.S. Application Data

(60) Provisional application No. 61/248,282, filed on Oct. 2, 2009, provisional application No. 61/185,492, filed on Jun. 9, 2009.

(51) Int. Cl.
 *C10J 3/54* (2006.01)
 *C01B 3/22* (2006.01)
 (Continued)

(52) U.S. Cl.
 CPC ... *C10J 3/54* (2013.01); *C01B 3/22* (2013.01); *C01B 3/34* (2013.01); *C07C 29/15* (2013.01);
 (Continued)

(58) Field of Classification Search
 CPC ...... C10J 3/54; C10J 3/485; C10J 2300/0916; C10J 2300/1292; C10J 2300/1693
 USPC ........................................................... 48/61
 See application file for complete search history.

(56) References Cited

U.S. PATENT DOCUMENTS

| 1,508,464 | A | | 9/1924 | McFarland |
| 2,237,491 | A | * | 4/1941 | Kutz ............................. 209/397 |

(Continued)

FOREIGN PATENT DOCUMENTS

| JP | 2002/012877 A | 1/2002 |
| SU | 1763814 A1 | 9/1992 |

(Continued)

OTHER PUBLICATIONS

International Preliminary Report on Patentability for International Application No. PCT/US10/37911, dated Dec. 12, 2011, 9 pages.

(Continued)

*Primary Examiner* — Matthew Merkling
(74) *Attorney, Agent, or Firm* — Rutan & Tucker, LLP

(57) ABSTRACT

A method, apparatus, and system for a solar-driven bio-refinery that may include a entrained-flow biomass feed system that is feedstock flexible via particle size control of the biomass. Some embodiments include a chemical reactor that receives concentrated solar thermal energy from an array of heliostats. The entrained-flow biomass feed system can use an entrainment carrier gas and supplies a variety of biomass sources fed as particles into the solar-driven chemical reactor. Biomass sources in a raw state or partially torrified state may be used, as long as parameters such as particle size of the biomass are controlled. Additionally, concentrated solar thermal energy can drive gasification of the particles. An on-site fuel synthesis reactor may receive the hydrogen and carbon monoxide products from the gasification reaction use the hydrogen and carbon monoxide products in a hydrocarbon fuel synthesis process to create a liquid hydrocarbon fuel.

19 Claims, 9 Drawing Sheets

(51) Int. Cl.

| | | |
|---|---|---|
| *C01B 3/34* | (2006.01) | |
| *C07C 29/15* | (2006.01) | |
| *C10J 3/00* | (2006.01) | |
| *C10G 2/00* | (2006.01) | |
| *C10J 3/48* | (2006.01) | |
| *C10J 3/72* | (2006.01) | |
| *F24J 2/07* | (2006.01) | |
| *C10J 3/56* | (2006.01) | |

(52) U.S. Cl.
CPC ... *C10G 2/30* (2013.01); *C10J 3/00* (2013.01); *C10J 3/482* (2013.01); *C10J 3/485* (2013.01); *C10J 3/56* (2013.01); *C10J 3/723* (2013.01); *F24J 2/07* (2013.01); *C01B 2203/0216* (2013.01); *C01B 2203/061* (2013.01); *C01B 2203/84* (2013.01); *C10G 2300/1014* (2013.01); *C10G 2300/1025* (2013.01); *C10G 2300/807* (2013.01); *C10J 2200/09* (2013.01); *C10J 2300/0906* (2013.01); *C10J 2300/0909* (2013.01); *C10J 2300/0916* (2013.01); *C10J 2300/0973* (2013.01); *C10J 2300/0989* (2013.01); *C10J 2300/1284* (2013.01); *C10J 2300/1292* (2013.01); *C10J 2300/1621* (2013.01); *C10J 2300/1659* (2013.01); *C10J 2300/1665* (2013.01); *C10J 2300/1693* (2013.01); *Y02B 40/18* (2013.01); *Y02E 10/41* (2013.01); *Y02E 50/18* (2013.01); *Y02E 50/32* (2013.01)

(56) References Cited

U.S. PATENT DOCUMENTS

| | | |
|---|---|---|
| 4,164,123 A | 8/1979 | Smith |
| 4,219,492 A | 8/1980 | Konoki et al. |
| 4,247,755 A | 1/1981 | Smith, Jr. et al. |
| 4,415,339 A | 11/1983 | Aiman et al. |
| 4,455,153 A | 6/1984 | Jakahi |
| 4,552,741 A | 11/1985 | Melchior |
| 4,704,137 A | 11/1987 | Richter |
| 4,756,722 A | 7/1988 | Knop et al. |
| 4,766,154 A | 8/1988 | Bonnell et al. |
| 5,179,129 A | 1/1993 | Studer |
| 5,581,998 A | 12/1996 | Craig |
| 5,618,500 A | 4/1997 | Wang |
| 5,647,877 A | 7/1997 | Epstein |
| 5,906,799 A | 5/1999 | Burgie et al. |
| 6,402,988 B1 | 6/2002 | Gottzmann et al. |
| 6,660,244 B2 | 12/2003 | Negishi et al. |
| 6,676,716 B2 | 1/2004 | Fujimura et al. |
| 6,872,378 B2 | 3/2005 | Weimer et al. |
| 7,033,570 B2 | 4/2006 | Weimer et al. |
| 7,207,327 B2 | 4/2007 | Litwin et al. |
| 7,553,476 B2 | 6/2009 | Marrella et al. |
| 7,632,476 B2 | 12/2009 | Shah et al. |
| 7,686,856 B2 | 3/2010 | Hemmings et al. |
| 7,856,829 B2 | 12/2010 | Shah et al. |
| 7,871,457 B2 | 1/2011 | Shah et al. |
| 7,881,825 B2 | 2/2011 | Esposito et al. |
| 7,931,888 B2 | 4/2011 | Drnevich et al. |
| 7,985,399 B2 | 7/2011 | Drnevich et al. |
| 8,007,761 B2 | 8/2011 | Drnevich et al. |
| 8,378,151 B2 | 2/2013 | Perkins et al. |
| 8,709,112 B2 | 4/2014 | Hilton et al. |
| 8,771,387 B2 | 7/2014 | Simmons et al. |
| 9,011,560 B2 | 4/2015 | Simmons et al. |
| 2002/0134019 A1 | 9/2002 | Paisley |
| 2003/0182861 A1 | 10/2003 | Weimer et al. |
| 2003/0208959 A1 | 11/2003 | Weimer et al. |
| 2003/0213514 A1 | 11/2003 | Ortabasi |
| 2004/0170210 A1 | 9/2004 | Do et al. |
| 2004/0219079 A1 | 11/2004 | Hagen et al. |
| 2005/0020700 A1 | 1/2005 | Bahnisch |
| 2005/0142049 A1 | 6/2005 | Amsden et al. |
| 2006/0024538 A1 | 2/2006 | Steinberg |
| 2006/0096298 A1 | 5/2006 | Barnicki et al. |
| 2006/0140848 A1 | 6/2006 | Weimer et al. |
| 2006/0188433 A1 | 8/2006 | Weimer et al. |
| 2006/0225424 A1 | 10/2006 | Elliott et al. |
| 2007/0098602 A1 | 5/2007 | Haueter et al. |
| 2007/0129450 A1 | 6/2007 | Barnicki et al. |
| 2007/0225382 A1 | 9/2007 | Van Den Berg et al. |
| 2008/0022595 A1* | 1/2008 | Lemaire et al. ............... 48/209 |
| 2008/0025884 A1 | 1/2008 | Tonkovich et al. |
| 2008/0057366 A1 | 3/2008 | Katikaneni et al. |
| 2008/0086946 A1 | 4/2008 | Weimer et al. |
| 2008/0104003 A1 | 5/2008 | Macharia et al. |
| 2008/0209891 A1 | 9/2008 | Johannes et al. |
| 2008/0222955 A1 | 9/2008 | Jancker et al. |
| 2008/0223214 A1 | 9/2008 | Palamara et al. |
| 2008/0284401 A1 | 11/2008 | Oettinger et al. |
| 2008/0293132 A1 | 11/2008 | Goldman et al. |
| 2008/0302670 A1 | 12/2008 | Boyle |
| 2008/0307703 A1 | 12/2008 | Dietenberger et al. |
| 2009/0013601 A1 | 1/2009 | Mandich et al. |
| 2009/0014689 A1 | 1/2009 | Klepper et al. |
| 2009/0018221 A1 | 1/2009 | Klepper et al. |
| 2009/0018222 A1 | 1/2009 | Klepper et al. |
| 2009/0018371 A1 | 1/2009 | Klepper et al. |
| 2009/0018372 A1 | 1/2009 | Tirmizi et al. |
| 2009/0064578 A1 | 3/2009 | Theegala |
| 2009/0069452 A1 | 3/2009 | Robota |
| 2009/0069609 A1 | 3/2009 | Kharas et al. |
| 2009/0093555 A1 | 4/2009 | Stites et al. |
| 2009/0151251 A1 | 6/2009 | Manzer et al. |
| 2009/0151253 A1 | 6/2009 | Manzer et al. |
| 2009/0156392 A1 | 6/2009 | Kharas |
| 2009/0156393 A1 | 6/2009 | Kharas |
| 2009/0156697 A1 | 6/2009 | Kharas |
| 2009/0313886 A1 | 12/2009 | Hinman |
| 2009/0318573 A1 | 12/2009 | Stites et al. |
| 2010/0000874 A1 | 1/2010 | Hinman |
| 2010/0022806 A1 | 1/2010 | Meitzner |
| 2010/0075837 A1 | 3/2010 | Meitzner et al. |
| 2010/0076228 A1 | 3/2010 | Alsum et al. |
| 2010/0099925 A1 | 4/2010 | Kharas |
| 2010/0099926 A1 | 4/2010 | Kharas |
| 2010/0099927 A1 | 4/2010 | Kharas |
| 2010/0137459 A1 | 6/2010 | Stites et al. |
| 2010/0152497 A1 | 6/2010 | Stites |
| 2010/0152498 A1 | 6/2010 | Kharas et al. |
| 2010/0210741 A1 | 8/2010 | Kharas |
| 2010/0212220 A1 | 8/2010 | Tirmizi |
| 2010/0237291 A1 | 9/2010 | Simmons |
| 2010/0242352 A1 | 9/2010 | Perkins et al. |
| 2010/0242353 A1 | 9/2010 | Jovanovic |
| 2010/0242354 A1 | 9/2010 | Perkins et al. |
| 2010/0243961 A1 | 9/2010 | Hilton et al. |
| 2010/0247387 A1 | 9/2010 | Perkins et al. |
| 2010/0249251 A1 | 9/2010 | Hilton et al. |
| 2010/0249468 A1 | 9/2010 | Perkins et al. |
| 2010/0270505 A1 | 10/2010 | Gallaspy et al. |
| 2010/0273899 A1 | 10/2010 | Winter |
| 2010/0280287 A1 | 11/2010 | Kharas et al. |
| 2010/0303692 A1 | 12/2010 | Perkins et al. |
| 2010/0331581 A1 | 12/2010 | Kharas et al. |
| 2011/0107661 A1 | 5/2011 | Tirmizi et al. |
| 2011/0107662 A1 | 5/2011 | Tirmizi et al. |
| 2011/0107663 A1 | 5/2011 | Tirmizi et al. |
| 2011/0124927 A1 | 5/2011 | Stites et al. |
| 2011/0155958 A1 | 6/2011 | Winter et al. |
| 2011/0301732 A1 | 12/2011 | Gao et al. |
| 2012/0181483 A1 | 7/2012 | Perkins et al. |
| 2012/0241677 A1 | 9/2012 | Perkins et al. |

FOREIGN PATENT DOCUMENTS

| | | |
|---|---|---|
| WO | WO 2010/144537 A9 | 12/2010 |
| WO | WO 2010/144540 A1 | 12/2010 |
| WO | WO 2010/144542 A1 | 12/2010 |
| WO | WO 2010/144544 A1 | 12/2010 |
| WO | WO 2010/144547 A1 | 12/2010 |

(56) References Cited

FOREIGN PATENT DOCUMENTS

| WO | WO 2010/144549 A1 | 12/2010 |
|---|---|---|
| WO | WO 2010/144552 A1 | 12/2010 |
| WO | WO 2010/144554 A1 | 12/2010 |
| WO | WO 2010/144556 A1 | 12/2010 |

OTHER PUBLICATIONS

International Preliminary Report on Patentability for International Application No. PCT/US10/37914, dated Dec. 12, 2011, 8 pages.
International Preliminary Report on Patentability for International Application No. PCT/US10/37923, dated Dec. 12, 2011, 13 pages.
International Preliminary Report on Patentability for International Application No. PCT/US10/37925, dated Dec. 12, 2011, 10 pages.
International Preliminary Report on Patentability for International Application No. PCT/US10/37930, dated Dec. 12, 2011, 13 pages.
International Preliminary Report on Patentability for International Application No. PCT/US10/37934, dated Dec. 12, 2011, 10 pages.
International Preliminary Report on Patentability for International Application No. PCT/US10/37938, dated Dec. 12, 2011, 10 pages.
International Preliminary Report on Patentability for International Application No. PCT/US10/37940, dated Dec. 12, 2011, 10 pages.
International Preliminary Report on Patentability for International Application No. PCT/US10/37944, dated Dec. 12, 2011, 10 pages.
Cross Reference to Related Applications Under 27 C.F.R. 1.78, 2 pages.
International Search Report for PCT/US10/037911, dated Aug. 6, 2010, 2 pages.
International Search Report for PCT/US10/037914, dated Aug. 13, 2010, 2 pages.
International Search Report for PCT/US10/037923, dated Aug. 9, 2010, 3 pages.
International Search Report for PCT/US10/037925, dated Aug. 10, 2010, 3 pages.
International Search Report for PCT/US10/037930, dated Sep. 20, 2010, 5 pages.
International Search Report for PCT/US10/037934, dated Aug. 9, 2010, 2 pages.
International Search Report for PCT/US10/037938, dated Aug. 5, 2010, 2 pages.
International Search Report for PCT/US10/037940, dated Aug. 13, 2010, 2 pages.
International Search Report for PCT/US10/037944, dated Aug. 18, 2010, 2 pages.
Munzinger, M., et al., "Biomass Gassification Using Solar Thermal Energy", *Anzses 2006*, pp. 1-10.
Mishra, Anuradha, et al., "Thermal Optimization of Solar Biomass Hybrid Cogeneration Plants", *Journal of Scientific & Industrial Research*, vol. 65, Apr. 2006, pp. 355-363.
Esser, Peter, et al., "The Photochemical Synthesis of Fine Chemicals With Sunlight," Angew. Chem. Int. Ed. Engl. 1994, vol. 33, pp. 2009-2023.
Written Opinion for International Application No. PCT/US2010/037923 mailed Aug. 9, 2010, 11 pages.
Restriction Requirement for U.S. Appl. No. 12/795,045 mailed Apr. 18, 2013, 5 pages. U.S. Patent and Trademark Office, Alexandria, Virginia USA.
Written Opinion for International Application No. PCT/US2010/037911 mailed Aug. 6, 2010, 7 pages.
Notice of Allowance for U.S. Appl. No. 12/796,121 mailed Oct. 11, 2012, 7 pages. U.S. Patent and Trademark Office, Alexandria, Virginia USA.
Non-Final Office Action for U.S. Appl. No. 12/796,121 mailed Jun. 7, 2012, 10 pages. U.S. Patent and Trademark Office, Alexandria, Virginia USA.
Written Opinion for International Application No. PCT/US2010/037914 mailed Aug. 13, 2010, 6 pages.
Written Opinion for International Application No. PCT/US2010/037925 mailed Aug. 10, 2010, 8 pages.
Restriction Requirement for U.S. Appl. No. 12/796,428 mailed Oct. 9, 2012, 7 pages. U.S. Patent and Trademark Office, Alexandria, Virginia USA.
Written Opinion for International Application No. PCT/US2010/037930 mailed Sep. 20, 2010, 11 pages.
Restriction Requirement for U.S. Appl. No. 12/796,471 mailed Mar. 13, 2013, 6 pages. U.S. Patent and Trademark Office, Alexandria, Virginia USA.
Written Opinion for International Application No. PCT/US2010/037934 mailed Aug. 9, 2010, 8 pages.
Restriction Requirement for U.S. Appl. No. 12/795,910 mailed Feb. 20, 2013, 6 pages. U.S. Patent and Trademark Office, Alexandria, Virginia USA.
Non-Final Office Action for U.S. Appl. No. 12/795,947 mailed Mar. 14, 2013, 26 pages. U.S. Patent and Trademark Office, Alexandria, Virginia USA.
Restriction Requirement for U.S. Appl. No. 12/795,947 mailed Oct. 9, 2012, 5 pages. U.S. Patent and Trademark Office, Alexandria, Virginia USA.
Non-Final Office Action for U.S. Appl. No. 12/795,989 mailed Jan. 24, 2013, 29 pages. U.S. Patent and Trademark Office, Alexandria, Virginia USA.
Written Opinion for International Application No. PCT/US2010/037940 mailed Aug. 13, 2010, 8 pages.
Written Opinion for International Application No. PCT/US2010/037944 mailed Aug. 18, 2010, 8 pages.
*Netscape Communications Corp. v. ValueClick, Inc.*, 684 F. Supp. 2d. 678—Dist, Court, ED Virginia 2010. No. 1:09cv225. United States District Court, E.D. Virginia, Alexandria Division. Oct. 22, 2009, 38 pages.
*Ex Parte* Wada and Murphy, U.S. Patent and Trademark Office Board of Patent Appeals and Interferences Decision on Appeal dated Jan. 14, 2008, 9 pages.
*Ex Parte* Chapman, U.S. Patent and Trademark Office Board of Patent Appeals and Interferences Decision on Appeal dated Feb. 9, 2012 for Appeal No. 2009-010238, U.S. Appl. No. 10/751,616, 6 pages.
Non-Final Office Action for U.S. Appl. No. 12/796,222 mailed Sep. 13, 2013, 7 pages. U.S. Patent and Trademark Office, Alexandria, Virginia USA.
Non-Final Office Action for U.S. Appl. No. 12/796,222 mailed Jan. 29, 2013, 48 pages. U.S. Patent and Trademark Office, Alexandria, Virginia USA.
Restriction Requirement for U.S. Appl. No. 12/796,319 mailed Jun. 20, 2013, 5 pages. U.S. Patent and Trademark Office, Alexandria, Virginia USA.
Non-Final Office Action for U.S. Appl. No. 12/796,471 mailed May 3, 2013, 22 pages. U.S. Patent and Trademark Office, Alexandria, Virginia USA.
Restriction Requirement for U.S. Appl. No. 12/795,947 mailed Oct. 9, 2013, 5 pages. U.S. Patent and Trademark Office, Alexandria, Virginia USA.
Final Office Action for U.S. Appl. No. 12/795,989 mailed Jul. 16, 2013, 28 pages. U.S. Patent and Trademark Office, Alexandria, Virginia USA.
Decision on Petition for the U.S. Appl. No. 12/796,045 mailed Jun. 22, 2010, 2 pages. U.S. Patent & Trademark Office, Alexandria, Virginia USA.
Decision on Petition for the U.S. Appl. No. 12/795,910 mailed Jun. 22, 2010, 2 pages. U.S. Patent & Trademark Office, Alexandria, Virginia USA.
Non-Final Rejection Action for U.S. Appl. No. 13/254,020 mailed May 9, 2013, 20 pages. U.S. Patent & Trademark Office, Alexandria, Virginia USA.
International Search Report and Written Opinion for International Patent Application No. PCT/US 10/59564, dated Mar. 2, 2011, 12 pages. International Searching Authority/US Alexandria, Virginia, USA.
Notification Concerning Transmittal of International Preliminary Report on Patentability for International Patent Application No. PCT/US2010/059564, dated Dec. 20, 2012, 10 pages. The International Bureau of WIPO, Geneva, Switzerland.

(56) References Cited

OTHER PUBLICATIONS

Bridgwater, et al., "Fast Pyrolysis Processes for Biomass," Renewable and Sustainable Energy Reviews, vol. 4, No. 1, 73 pages, Mar. 2000.
Lede, "Solar Thermochemical Conversion of Biomass", Solar Energy, vol. 65, No. 1, 11 pages, Jan. 1, 1999.
International Search Report and Written Opinion, International Patent Application No. PCT/US2013/033773, dated Jun. 18, 2013, 14 pages. International Searching Authority/US, Alexandria, Virginia, USA.
Restriction Action for U.S. Appl. No. 13/254,020 mailed Nov. 26, 2012, 6 pages. U.S. Patent & Trademark Office, Alexandria, Virginia USA.
Final Office Action for U.S. Appl. No. 12/796,222 mailed Jul. 19, 2013, 34 pages. U.S. Patent & Trademark Office, Alexandria, Virginia USA.
Office Action for Chinese Patent Application No. 201080017429.1 mailed Aug. 2, 2013, 10 pages, State Intellectual Property Office of PRC.
Notice of Allowance for U.S. Appl. No. 12/796,045, mailed Feb. 28, 2014, 12 pages.
First Examination Report for Australian Patent Application No. 2010258840 mailed Nov. 19, 2014; 3 pages.
Second Office Action for Chinese Patent Application No. 201080017429.1 mailed Jan. 28, 2014, 6 pages.
Third Office Action for Chinese Patent Application No. 201080017429.1 mailed May 23, 2014, 9 pages.
First Examination Report for Australian Patent Application No. 2010258845 mailed Nov. 8, 2014, 3 pages.
Notice of Allowance for U.S. Appl. No. 12/796,319 mailed Dec. 9, 2013, 19 pages.
First Office Action for Australian Patent Application No. 2010258847 mailed Nov. 13, 2014, 3 pages.
Final Office Action for U.S. Appl. No. 12/796,471 mailed Nov. 12, 2014, 28 pages.
Final Office Action for U.S. Appl. No. 12/796,471 mailed Nov. 27, 2013, 26 pages.
Non-Final Office Action for U.S. Appl. No. 12/796,471 mailed Jun. 25, 2014, 23 pages.
Advisory Action for U.S. Appl. No. 12/796,471 mailed Mar. 5, 2015, 6 pages.
Advisory Action for U.S. Appl. No. 12/796,471 mailed Mar. 10, 2014, 4 pages.
First Office Action for Australian Patent Application No. 2010258852 mailed Nov. 14, 2014, 3 pages.
Notice of Allowance for U.S. Appl. No. 12/795,910 mailed Nov. 20, 2014, 25 pages.
First Office Action for Australian Patent Application No. 2010258855 mailed Nov. 20, 2014, 3 pages.
Office Action for Chinese Patent Application No. 201080024924.5 mailed Feb. 24, 2014, 9 pages.
Office Action for Chinese Patent Application No. 201080024924.5 mailed Aug. 29, 2014, 12 pages.
Advisory Action for U.S. Appl. No. 12/795,947 mailed Jan. 21, 2014, 4 pages.
Non-Final Action for for U.S. Appl. No. 12/795,947 mailed Jun. 3, 2014, 30 pages.
Non-Final Action for for U.S. Appl. No. 12/795,947 mailed Sep. 15, 2014, 31 pages.
Office Action for Australian Patent Application No. 2010258857 mailed Sep. 24, 2014, 3 pages.
Notice of Reexamination for Chinese Patent Application No. 201080025216.3 mailed Feb. 9, 2015, 9 pages.
Office Action for Chinese Patent Application No. 201080025216.3 mailed Mar. 27, 2014, 9 pages.
Office Action for Chinese Patent Application No. 201080025216.3 mailed Jun. 27, 2014, 10 pages.
Notice of Allowance Office Action for U.S. Appl. No. 13/254,020 mailed Dec. 3, 2014, 7 pages.
Non-Final Office Action for U.S. Appl. No. 13/254,020 mailed Jun. 16, 2014, 28 pages.
Final Office Action for U.S. Appl. No. 13/254,020 mailed Oct. 29, 2013, 23 pages.
Office Action for Australian Patent Application No. 2010/355257 mailed Feb. 10, 2015, 4 pages.
Non-Final Office Action for U.S. Appl. No. 13/429,752 mailed Feb. 20, 2015, 25 pages.
Restriction Action for U.S. Appl. No. 13/429,752 mailed Oct. 1, 2014, 5 pages.

* cited by examiner

Multiple tube reactor

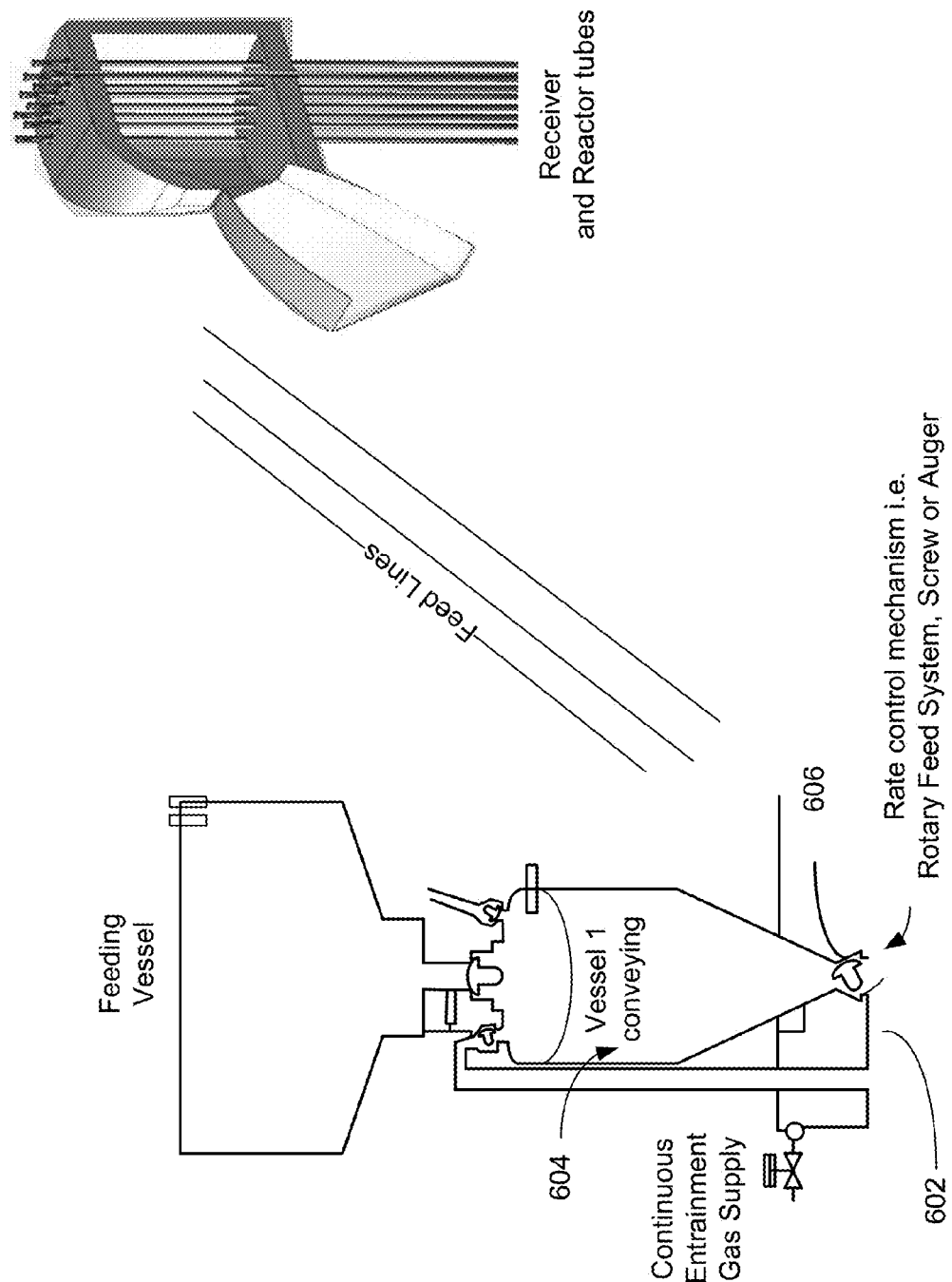

SYSTEMS AND METHODS FOR BIOMASS GRINDING AND FEEDING

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD OF THE INVENTION

Embodiments of the invention generally relate to systems, methods, and apparatus for refining biomass and other materials. More particularly, an aspect of an embodiment of the invention relates to solar-driven systems, methods, and apparatus for refining biomass and other materials.

BACKGROUND OF THE INVENTION

Biomass gasification is an endothermic process; energy must be put into the process to drive it forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. In contrast, the proposed solar-driven biorefinery uses the external source of energy (solar) to provide the energy required for reaction, so none of the biomass need be consumed to achieve the conversion. This results in significantly higher yields of gallons of gasoline per biomass ton than other technologies. As the energy source being used to drive the conversion is renewable and carbon free. Also, chemical reactors are generally engineered to operate at constant conditions around the clock rather than on a cyclic basis.

SUMMARY OF THE INVENTION

Some embodiments relate to a solar-driven bio-refinery with an entrained-flow biomass feed system. The system may be feedstock flexible via at least particle size control of the biomass refined. One example system includes a chemical reactor and an on-site fuel synthesis reactor. The chemical reactor may be aligned to receive concentrated solar thermal energy from an array of heliostats, solar concentrating dishes, or a combination of both. This energy can be used to refine the biomass.

In some embodiments, the entrained-flow biomass feed system uses an entrainment carrier gas and supplies a variety of biomass sources fed as particles into the solar-driven chemical reactor. The variety of biomass sources may include three or more types of biomass that can be fed, individually or in combinational mixtures as long as a few parameters are controlled, including particle size of the biomass supplied by the feed lines, without having to change the components making up the feed system. These sources can include rice straw, rice hulls, corn stover, switch grass, non-food wheat straw, miscanthus, orchard wastes, sorghum, forestry thinning, forestry wastes, source separated green wastes and other similar biomass sources. Additionally, the biomass sources may be used in a raw state or partially torrified state as long as a few parameters are controlled such as the particle size. In some cases, food stock biomass might also be processed.

One or more feeding vessels are in the biomass feed system to each supply a tube subset of two or more reactor tubes in the solar-driven chemical reactor. The feeding vessel has one or more outlets configured to supply a consistent volumetric amount of biomass particles within 10 percent of the demand signal amount when distributing biomass particles to the two or more reactor tubes.

In some embodiments, concentrated solar thermal energy drives gasification of the particles of the biomass to generate at least hydrogen and carbon monoxide products from the gasification reaction.

BRIEF DESCRIPTION OF THE DRAWINGS

The drawings refer to embodiments of the invention in which:

FIGS. 6a and 6b illustrate block diagrams of embodiments of a feed system;

Figure 1:
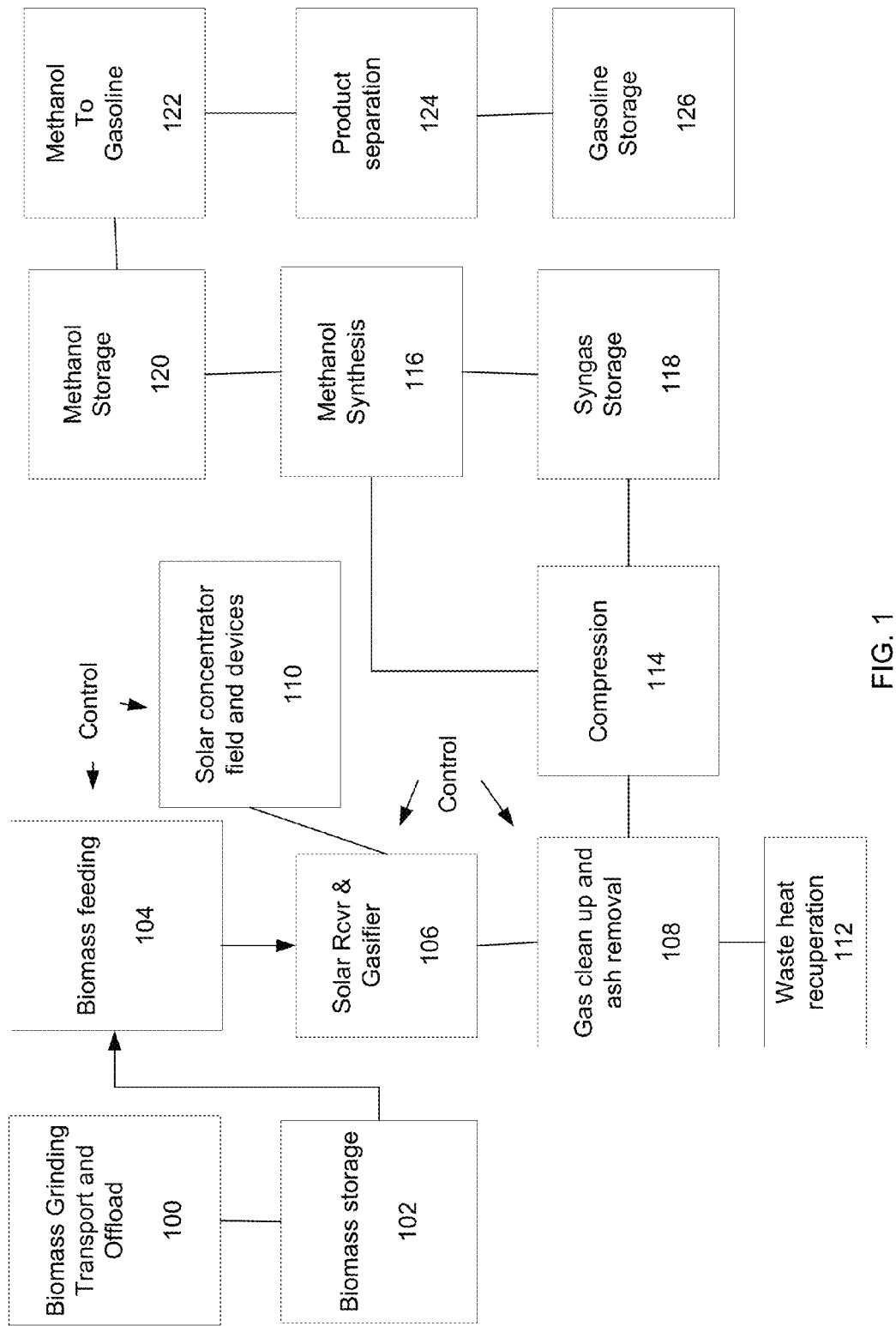
FIG. 1 illustrates a block diagram of an embodiment of an example process flow.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references, such as first reactor tube, may be made. However, the specific numeric reference should not be interpreted as a literal sequential order but rather interpreted that the first reactor tube is different than a second reactor tube. Thus, the specific details set forth are merely exemplary. The specific details may be varied from and still be contemplated to be within the spirit and scope of the present invention. The term coupled is defined as meaning connected either directly to the component or indirectly to the component through another component.

In general, the solar-driven bio-refinery includes an entrained-flow biomass feed system. The system may be feedstock flexible via at least particle size control of the biomass without having to change the components making up the feed system. One example system includes a chemical reactor, one or more a feeding vessels, and an on-site fuel synthesis reactor. The chemical reactor may receive concentrated solar thermal energy from an array of heliostats and this energy can be used to refine the biomass. A heliostat is generally a device that tracks the movement of the sun and typically utilizes a mirror to redirect sunlight toward a stationary target or receiver such as a solar thermal tower.

Some embodiments relate to the entrained-flow biomass feed system that uses an entrainment carrier gas and supplies a variety of biomass sources fed as particles into the solar-driven chemical reactor. The variety of biomass sources may include three or more types of biomass that can be fed, individually or in combinational mixtures. These sources can include rice straw, rice hulls, corn stover, switch grass, non-food wheat straw, miscanthus, orchard wastes, forestry wastes, sorghum, source separated green wastes and other similar biomass sources. Additionally, the biomass sources may be used in a raw state or partially torrefied state as long as a few parameters are controlled such as the particle size. A feeding vessel, such as a lock hopper, in the biomass feed system supplies a tube subset of two or more reactor tubes in the solar-driven chemical reactor. Although this design applies to a wide variety of chemical reactors, this discussion for sake of brevity and clarity focuses on the synthesis of methanol from syngas.

In some embodiments, concentrated solar thermal energy drives gasification of the particles of the biomass to generate at least hydrogen and carbon monoxide products from the gasification reaction.

FIG. 1 illustrates a block diagram of an embodiment of an example process flow. Some embodiments encompass a solar-driven-biomass gasification to liquid fuel/electrical process. The process might also include generation, chemical processing, or bio-char, for solar generated syngas derivative product or other similar technical process. In a specific example implementation the process described is a solar-driven-biomass gasification to 'green' liquid fuel process. In an embodiment, this process includes one or more of the following process steps.

Biomass grinding or densification, transport, and then off-load 100 may be part of the overall process. Bales of the biomass can be compressed and densified by a compactor to facilitate transport to on-site via the densification achieved by the compression and the bales are sized to dimensions that may, for example, fit within a standard box car size or shipping container size to fit within standard compactor size. The entrained-flow biomass feed system can be preceded by a grinding system equipped with mechanical cutting device and a particle classifier, such as a perforated screen or a cyclone, to control the size of the particles that are then fed into and gasified in the solar-driven chemical reactor.

Equipment generally used for grinding biomass includes impact mills (e.g. hammer mills), attrition mills, and kinetic disintegration mills-KDS (e.g. flail mills). A hammer mill system, KDS, or similar system can be used to grind the bales (loaded by conveyer) into particles, which are to be fed into the solar thermal gasifier. The ground particles have an average screen size between 500 microns (um) and 1000 um in diameter, and are loaded into, a silo with a standard belt conveyer or with a positive or negative pressure pneumatic conveying system. The ground particles may also have an average screen size between 50 microns (um) and 1000 um, 50 microns (um) and 200 um, 50 microns (um) and 2000 um and various combinations.

The biomass may then be stored 102. As needed, the biomass will be fed 104 into an example solar-driven chemical reactor via a feed system. For example, after grinding and pulverizing the biomass to particles, a lock-hopper feed system feeds the particles of biomass into the solar-driven chemical reactor to be gasified. The feed system can supply the variety and types of biomass particles discussed above.

A solar receiver and gasifier 106 may be used to thermally decompose the biomass. An example biomass gasifier design and operation can include a solar chemical reactor and solar receiver to generate components of syngas. Various heliostat field designs and operations to drive the biomass gasifier might be used. Some example designs may include a solar concentrator, secondary concentrator, focused mirror array, etc. to drive biomass gasifier 110.

Quenching, gas clean up, and ash removal from biomass gasifier 108 may be provided for. Some non-pilot syngas may exit the system 112. Some gasses may be a waste product, while other gasses can be compressed 114 prior to storage 118 or e.g., methanol synthesis 116. Methanol may then be stored 120 for later methanol to gasoline conversion 122.

In various embodiments, synthesis gas may be feed to another technical application. Examples include a syngas to other chemical conversion process. The other chemical of chemicals produced can include liquefied fuels such as transportation liquefied fuels. Some transportation liquefied fuels include jet fuel, DME, gasoline, diesel, and mixed alcohol, bio-char with a high sequestered amount of carbon; chemical production, electricity generation, synthetic natural gas production, heating oil generation, and other similar syngas based technical applications. In an example hydrocarbon based fuel, e.g., methanol, 116 may be formed from syngas. The methanol may be further converted to gasoline or other fuels 122 and various products may be separated out from the gasoline 124 or syngas. These products, e.g., gasoline, may then be stored for later use as an energy source.

In one example, the solar-driven biorefinery may have a throughput of no less than one dry ton per day of cellulosic biomass from a region with abundant sources, such as California, that will produce "green" gasoline. Solar thermal energy may be used to drive gasification of biomass, upgrading the heating value of the feedstock with a renewable energy source, while allowing operation at temperatures where tar formation is negligible. Feedstock carbon yield to "green" gasoline is estimated to be at least 30% higher in comparison to conventional thermochemical partial gasification processes since none of the biomass is oxidized for heating value. Synthesis gas will be processed using proven catalytic processes into intermediate methanol, and then subsequently into gasoline via the MTG process. Alternatively the product gas will be catalytically converted into a liquid fuel such as transportation diesel or aviation fuels via GTL Fischer-Tropsch process. The biorefinery may be built in an area having ample solar irradiation and proximity to a variety of biomass feed stocks.

In one embodiment, an on-site fuel synthesis reactor has an input to receive the hydrogen and carbon monoxide products from the gasification reaction and configured to use the hydrogen and carbon monoxide products in a hydrocarbon fuel synthesis process to create a liquid hydrocarbon fuel. For example, synthesis gas may be processed using many different technical applications as discussed above. For example the solar generated syngas can be used with proven catalytic processes into intermediate methanol, and then subsequently into gasoline via the MTG process. In one embodiment, the biorefinery will be the first solar unit integrated with a downstream liquid transportation fuels plant. Thus, the fuel synthesis reactor may be geographically located on the same site as the chemical reactor and integrated into the process to utilize the hydrogen and carbon monoxide products from the gasification reaction.

In some embodiments, the entrained-flow biomass feed system 104 includes a computerized control system configured to balance the amount of biomass particles flowing in each of the reactor tubes to an amount of solar energy available. For example, a 2-phase control system receives a signal from the computerized control system to control flow in the individual reactor tubes by controlling a rotational rate of a screw of a lock hopper feeding the biomass, a rotational rate of airlock type metering device, changing an amount of reactor tubes participating in the gasification reaction, controlling an amount of output/ports supplying biomass, an amount of compression of a flexible pipe section applied to each individual feed line that the biomass particles are flowing through, and other example combinations. As noted, these biomass feedstock resources can include energy crops such as miscanthus and switchgrass, which are high-impact and high-yield energy crops. A biomass with low lignin content will make it easier to gasify and process in the solar gasifier.

Moving the biomass from the field into the reaction zone of the solar gasifier can include a number of steps, such as biomass densification, biomass transport, biomass offload, and biomass storage.

The biomass, such as rice straw, corn stover, high biomass sorghum, switchgrass, miscanthus, bales can be compressed to make transportation via the densification more economical. Compression allows very high loadings on the train cars and trucks.

Transport biomass to site 100 occurs 1) with the biomass aggregated in the field as bales, 2) the bales are then compressed, and 3) these bales are loaded into shipping containers for transport. Alternatively, torrefaction of the biomass may be implemented to densify energy content per unit weight of biomass hence reduce the effective shipping cost. Physical location in U.S. may play a large part in what feedstock we use due to shipping and availability issues. The bales are loaded into standard shipping containers by forklift and transported by rail to the site. The densification achieved by compression allows high loadings on the train cars and/or trucks, greatly reducing transportation costs. This allows lower cost transportation of biomass from highly fertile regions to the arid desert regions where the solar facilities will be located.

The biomass materials are offloaded at the plant site, ground in a hammer mill, and fed across a pressure barrier into the entrained flow reactor. At the solar-driven biorefinery, the biomass is unloaded and stored in a covered shed. The biomass storage is at the base of the solar tower for best accessibility to the grinding and the feeding systems. In some biomass, spoilage only occurs in 1%-3% of delivered straw and grass feed stocks. Spoilage will be tested in a delivery burn test at the primary grinding site, with rejection of spoiled biomass occurring before grinding.

Figure 2:
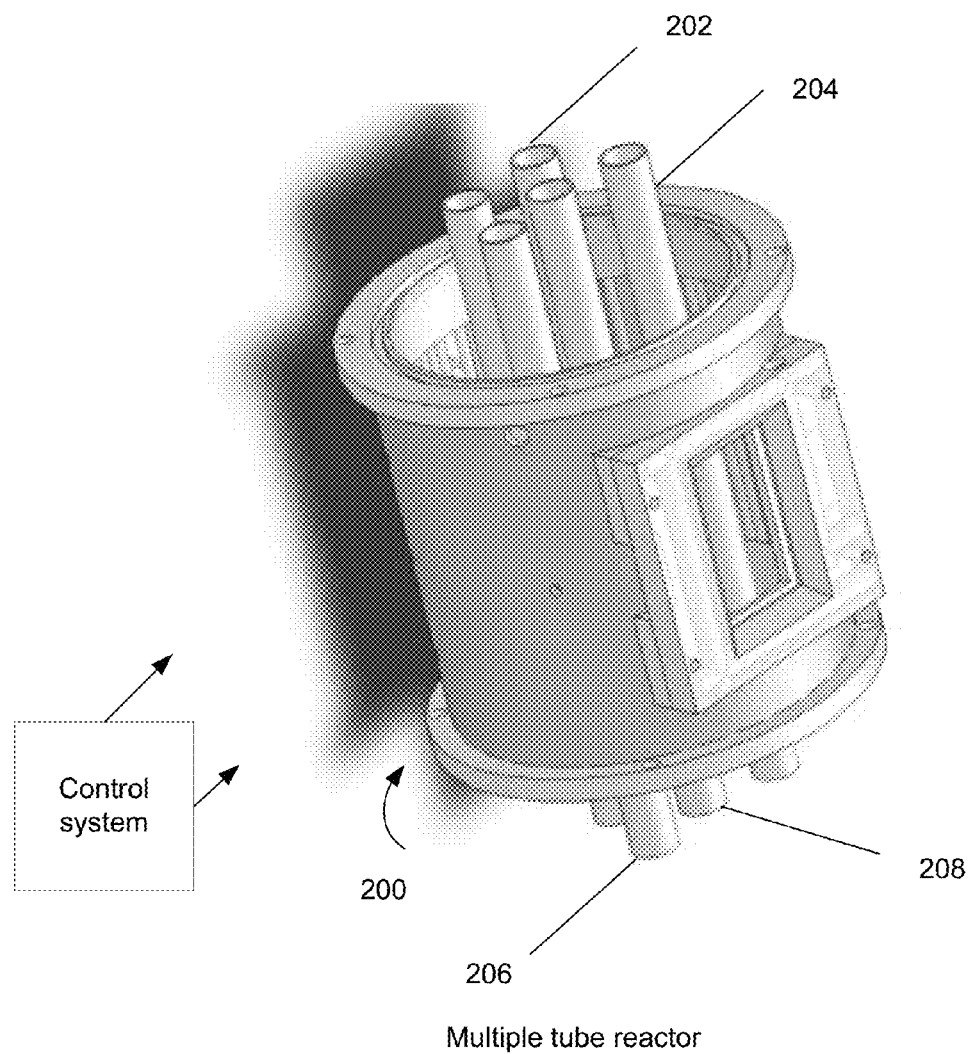
FIG. 2 illustrates a diagram of an embodiment of an example multiple tube reactor.

FIG. 2 illustrates a diagram of an example multiple tube chemical reactor 200 that may be used in a solar-driven system. Reactor 200 has multiple reactor tubes 202, 204, 206, 208 and a separate entrainment line may be used for each of the gasifier reactor tubes 202, 204, 206, 208 in the chemical reactor 200. This may allow for independent temperature control and balancing of the amount of particles of biomass flowing in each of the gasifier reactor tubes 202, 204, 206, 208 in the multiple-tube solar-driven chemical reactor 200.

Multiple example feeding vessels and systems will be described herein. An example system will be described below and more in FIG. 6. An objective of the feeding system is to feed as many reactor tubes as possible with the fewest number of feeding vessels such as lock-hopper systems. The lock hopper and injection vessels are pressure vessels, and thus expensive. Also, the more lock-hopper systems the system has, the distribution of ground particles of biomass then becomes more elaborate and complex.

An example lock hopper rotary feed system has an output to distribute the particles of biomass to the gasifier reactor tubes 202, 204, 206, 208. The rotary feed system, such as a Rotoscrew® in combination with a fluid bed splitter can allow for balanced feeding to individual reactor tubes 202, 204, 206, 208. An additional auger may be mounted in the lock hopper to aid the flow of the biomass into the Rotoscrew®. The feed rate of the biomass particles is controlled by a weight measuring metering device, such as load cells, and by the rotational speed of the Rotoscrew® set by a device such as variable frequency drive (VFD). The Rotoscrew® may be located at the base of the lock hopper and its rotational speed can be controlled by a computerized control system to respond to feed demand of the system. The control system may operate in a networked environment using logical connections to one or more remote computers, such as a remote computer. The control system hardware may be one or more of a Programmable Logic Controller, via different data communication protocols using Personal Computer, Macintosh, CNC, neural nets, analog devices, with accompanying software applications and algorithms scripted to perform various functions, or various combinations of these systems. In an embodiment, the computerized control system controls the feed rate of biomass particles in the solar-driven chemical reactor based on an amount of solar energy available indicated by sensors including temperature sensors and/or light meters, temperature of the reactor tubes indicated by one or more temperature sensors, particle size and type of biomass being used, and other parameters supplied to the computerized control system such as product yield and composition.

The system may be feedstock flexible because the gasification energy is external to the biomass itself. The biomass is not combusted, and a combustion reaction does not need to be managed at the same time as the gasification reaction; thus, eliminating the need for a specialized reactor geometry for each type of biomass.

The solar-driven bio-refinery can include a solar-driven chemical reactor that has a cyclic operation rather than a continuous steady state operation. One or more sensors indicate an amount of solar energy available during the cyclic operations. The computerized control system receives a feedback signal from a set of sensors, including the solar energy sensors. The computerized control system controls the feed rate of the particles of biomass material into the two or more reactor tubes with well controlled feed rates that respond to changing of the feed rate of the biomass material based on changing solar availability given as feedback to the computerized control system by the solar energy sensors.

Figure 3:
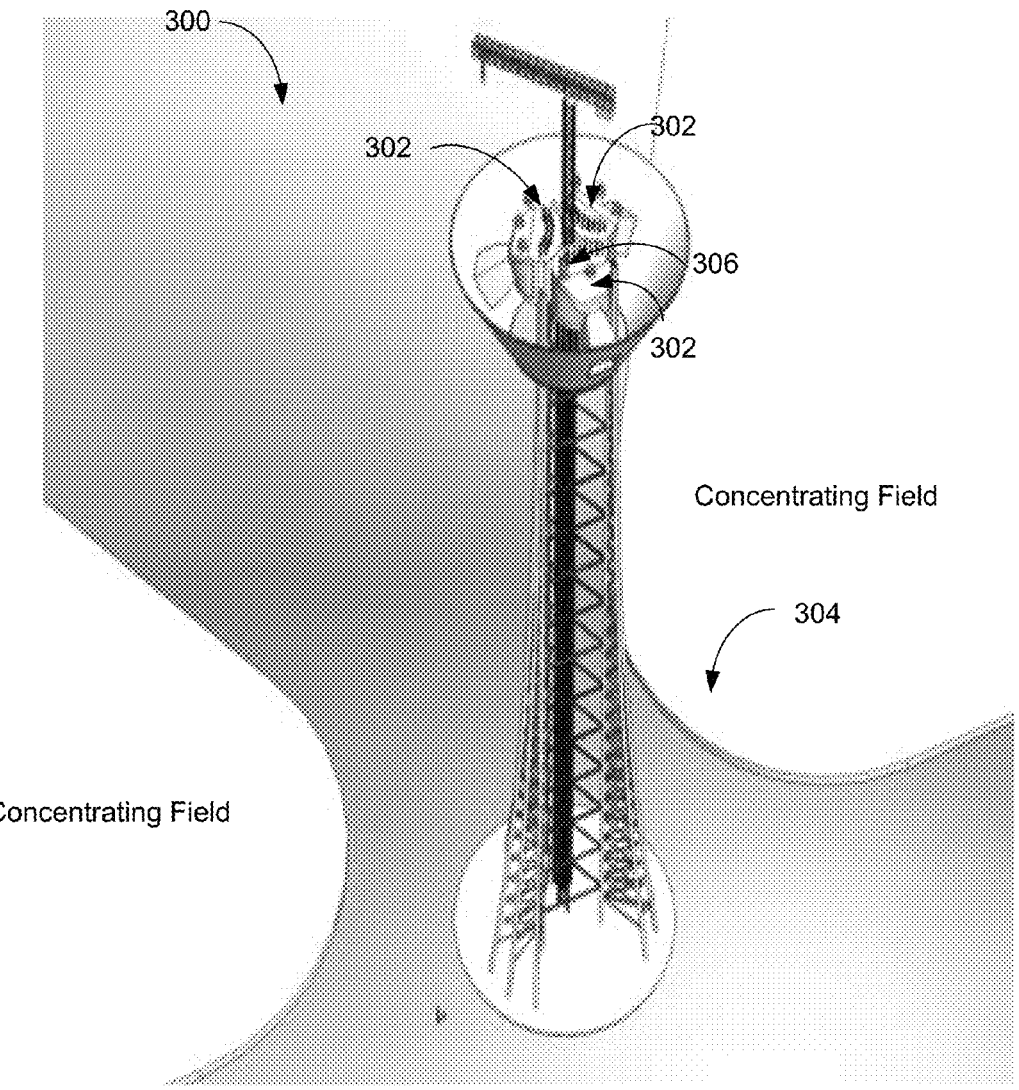
FIG. 3 illustrates a diagram of an embodiment of an example solar tower with receivers and heliostat field.

FIG. 3 illustrates a diagram of an example solar tower 300 with receivers 302 and heliostat field 304. In some embodiments solar tower 300 may be used to from a solar-driven bio-refinery with the entrained-flow biomass feed system.

The feed system can be feedstock flexible via, for example, particle size control of the biomass.

A solar-driven chemical reactor 306 receives concentrated solar thermal energy from an array of heliostats 304. The chemical reactor 306 can be, for example, a multiple reactor tube, downdraft chemical reactor, which receives concentrated solar thermal energy from the array of heliostats 306.

A solar tower 300 may form a portion of a solar-driven bio-refinery that may also include a biomass feed system that has balancing of the feed lines to each of the reactor tubes in a multiple tube chemical reactor. For example, biomass may be fed to the solar reactor in an operation including three parts: biomass transport and preparation for feeding to the solar tower reactor, biomass transport to the top of the, e.g., 500+ foot tower, and distribution into the specific downdraft tubes of the reactor. The distribution may be performed via multiple stages.

In some embodiments, the system uses an entrainment gas to convey particles from the ground into the tubes. In this design, that entrainment gas, which may be hydrocarbon gas, such as Low Pressure Gas (LPG), natural gas, methane, etc., $H_2O$ steam produced with energy recovered from waste heat in the plant, or $CO_2$ recycled from the amine unit, may be used as the purging gas in the lock hopper. The pressurization can be provided by for example, recycled carbon dioxide from the amine acid gas removal step or dry steam heated by waste heat from products coming out of the chemical reactor. The biomass may be pressurized up to 75 psig (15-75 psig range), for example. The pressurized biomass may then be entrained in the steam or other carrier gas, and fed up the tower to the solar thermal gasifier.

For example, the particles of biomass are pre-heated prior to entry into the chemical reactor by the entrainment carrier gas. The entrainment carrier gas is at least one of carbon dioxide gas and steam, which is heated by waste heat from the reaction products of the gasification reaction coming out of the chemical reactor by a counter flow heat exchanger using the waste heat as its heat source to heat the entrainment carrier gas up to a maximum temperature of 300 degrees C. The entrained-flow biomass feed system can include a computerized control system configured to balance the amount of biomass particles flowing in each of the reactor tubes to an amount of solar energy available via, for example, a 2-phase control system to control flow in the individual reactor tubes. One or more detectors may indicate to the computerized control system an amount of solar energy available in different areas of the chemical reactor to guide a distribution of the biomass particles flowing in each of the reactor tubes. Alternatively, the feed can be distributed evenly among the tubes within subsets of tubes and the biomass supply to the solar receiver can be controlled by engaging different numbers of tube subsets.

The control system balances the amount of biomass particles flowing into each of the reactor tubes to an amount of solar energy available by 1) controlling a rotational rate of a screw of a lock hopper feeding the biomass where all the tubes in the tube subset have their feed rate simultaneously turned up or turned down, 2) where of the multiple reactor tubes is split into two or more groups of tube subsets and varying an amount of the reactor tube-subsets participating in the gasification reaction by turning on or turning off a flow of particles of biomass from the feed vessel to the reactor tubes making up a tube subset, or 3) a combination of both.

In some embodiments, onsite biomass storage can have bales stored at the base of the solar tower for best accessibility to the feeding and grinding systems. Biomass bales are stored in a silo type structure with bale moisture content between 5-50% with a typical range between 10% and 14%. The biomass, such as rice straw, rice hulls, corn stover, etc. bales can be stored onsite in a Biomass Storage unit located at the base of the solar tower for best accessibility to the feeding system.

In some embodiments, the gasification of the biomass occurs in two phases. An important aspect of the initial phase of gasification is that it is relatively fast at low temperatures and extremely fast at high temperatures, with completion in 0.1-0.3 seconds at least 600° C. Thus, this primary phase can be completed quickly in the aerosol reactor, and the remaining char and tars can heat up to temperatures of at least 950° C. where their gasification can be completed. The char gasification phase is the slowest reaction step of the solar biomass gasification process but is possible with short residence times at these temperatures.

Figure 4:
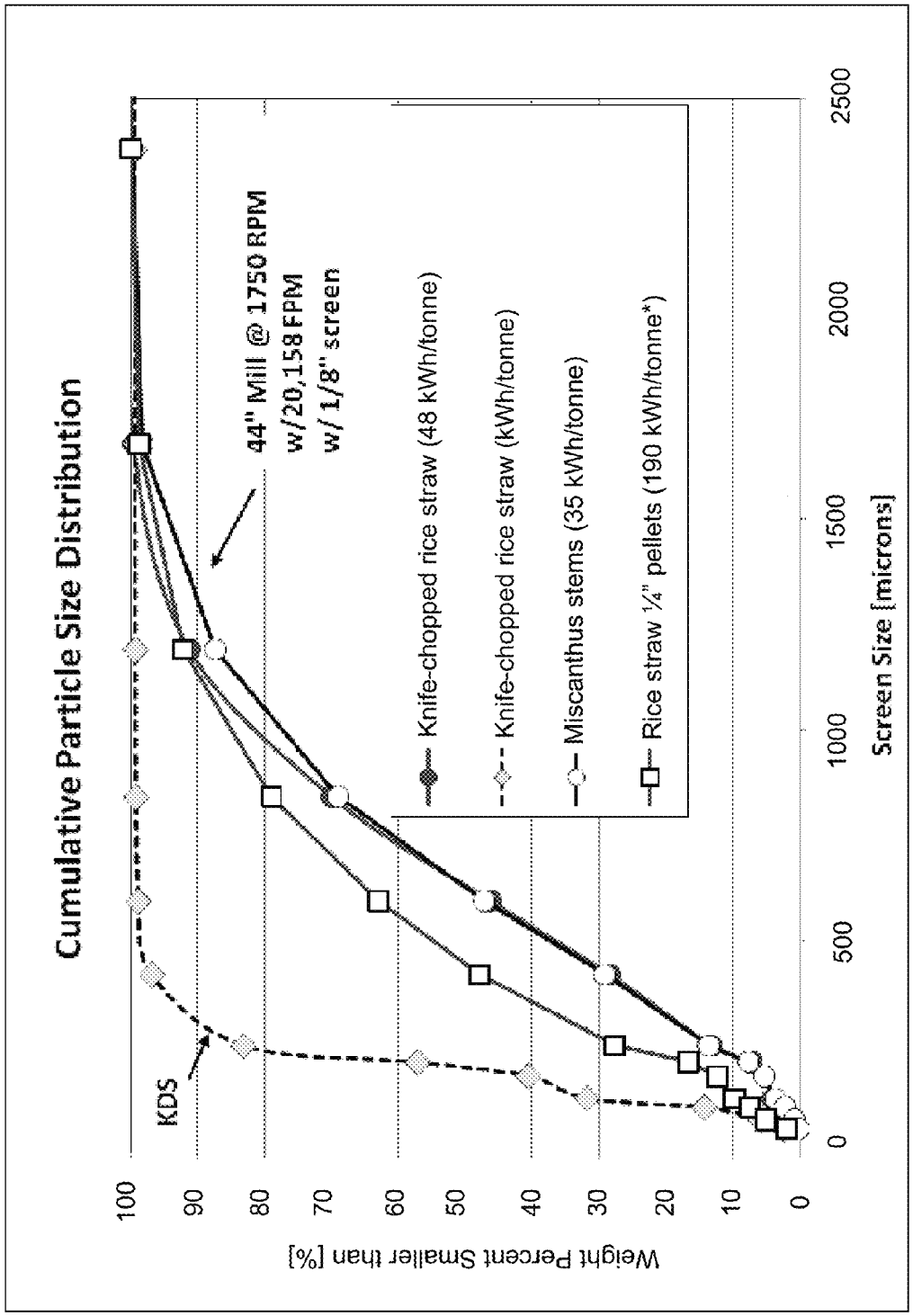
FIG. 4 illustrates a graph of an embodiment of particle size distribution of some example biomass types.

FIG. 4 illustrates cumulative particle size distributions. The graph illustrates the weight percentage below Y % for a given screen size in microns. Four example materials are illustrated with the corresponding milling power requirements: knife-chopped rice straw at 48 kilowatt-hours per ton in a hammer-mill, knife-chopped rice straw with an unknown energy value per ton in KDS, miscanthus stems at 35 kilowatt-hours per ton in a hammer-mill, and pelletized rice straw at 190 kilowatt-hours per ton including energy for both pelletization and grinding. The grinding system and the feed system may supply the various biomass types.

The smaller the size of the particle of the various types of biomass, the less difference in the way the feed system and reactor view particles from different types of biomass. The average size of ground particles may be correlated to filter particle size used in standard filter ranges.

Biomass particle size is a parameter that can impact performance of this solar-driven gasifier reactor. Through the mass transfer coefficient and residence time, biomass particle size controls intrinsic biomass reactivity and imposes specific solids handling constraints. In general, there is a trade-off between particle size range required by gasification kinetics, and the capital and operating costs associated with providing target biomass size reduction. In addition, the final material properties affect transportation cost (bulk density) as well as the cost of conveyers, bins, hoppers, and required energy for high pressure pneumatic transport. Based on the kinetic experiments described herein, the particle size required for the process may be generally between 50 um and 2000 um, for example.

The entrained-flow biomass feed system can include a gas source for an entrainment carrier gas and one or more feed lines to supply a variety of biomass sources that may be fed as particles into the solar-driven chemical reactor. In some embodiments, the variety of biomass sources feedable by the feed system without major configuration changes includes the below described three or more of the types of biomass.

The variety of biomass sources may include rice straw, rice hulls, corn stover, switch grass, non-food wheat straw, miscanthus, orchard wastes, forestry wastes, source separated green wastes and other similar biomass sources. These biomass sources may be in a raw state or partially (torrefied) state, as long as a few parameters such as particle size are controlled. Concentrated solar thermal energy can drive the gasification of the particles of the biomass in the solar-driven chemical reactor to generate hydrogen, carbon monoxide, and perhaps other gases from the gasification reaction.

The biomass may be fed into an example solar gasification system using an entrained-flow biomass feed system that includes a computerized control system. Such a computerized control system can control the biomass flow rate for the particle size, type of biomass, and current estimated temperature in each reactor tube. For example, the temperature may be selected to achieve from the gasification reaction a greater than 90 percent conversion of the biomass particles to at least hydrogen and carbon monoxide products with low to zero tar of less than 50 mg/Nm^3. In an embodiment, the tar content may be less than 200 mg/Nm^3.

The solar gasification process can be feedstock flexible and may be able to leverage a wide variety of biomass types. Generally, the reactor will be feedstock flexible as long as the particle size is controlled. The feed system is less sensitive to the type of feedstock used. Also, types of biomass can be selected based on parameters of the amount of moles of H2, CO, and CO2 gas produced from the gasification per ton, different ash content, and availability in quantity to be a renewable source of biomass to support consumption demands of transportation industry.

Figure 5:
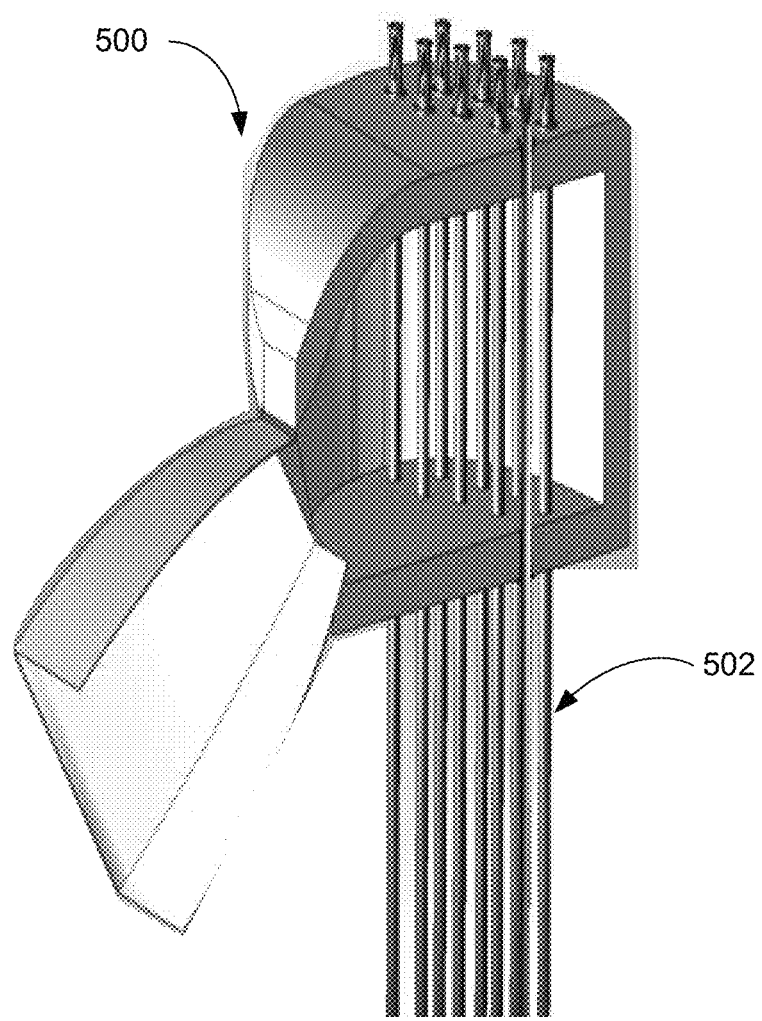
FIG. 5 illustrates a diagram of an embodiment of a solar thermal receiver with gasifier reactor tubes.

FIG. 5 illustrates a diagram of a solar thermal receiver 500 with gasifier reactor tubes 502. The solar thermal receiver 500 can form a portion of a solar-driven bio-refinery. In some embodiments, the solar thermal receiver 500 can be a solar-driven chemical reactor that has multiple reaction tubes in a downdraft orientation. Additionally, the feed system may feed biomass particles into the multiple reaction tubes 502, in which the particles of biomass may be gasified in the presence of steam in a gasification reaction zone at a temperature exceeding 950 degrees C. from the exit of the gasification reaction zone of the reactor tubes. At least hydrogen and carbon monoxide products are generated from the gasification reaction.

In some embodiments, the entrained-flow biomass feed system may include a device such as a Bulkmatology™ Pelletron Flow Enhancer™, which may control an amount of entrainment gas carrying the particles of biomass to a gasification reaction zone of the reactor tubes by leaking out a portion of the carrier gas just prior to an entrance to a gasification reaction zone of the reactor tubes, thereby increasing the biomass-to-carrier gas weight ratio at the entrance to the reactor tubes. For example, the entrained solids of biomass-to-carrier gas ratio at the entrance of the reactor tubes may be as much as three times its counterpart in the conveying lines upstream of Pelletron Flow Enhancer™.

In some embodiments, a reduction in the carrier gas flow rate can occur near the top of the reactor tubes in the downdraft solar thermal receiver allowing unimpeded inertia-driven flow of dispersed particles into the reactor tubes. Additionally, in various embodiments, an outlet of each of the feed lines can be configured to control a desired dispersion pattern of the biomass particles into its corresponding reactor tube to maximize radiation absorption by the particles when injected into the reactor tube based on a shape and width of the outlet of the feed line pipe carrying the biomass particles to its corresponding reactor tube.

Figure 6A:
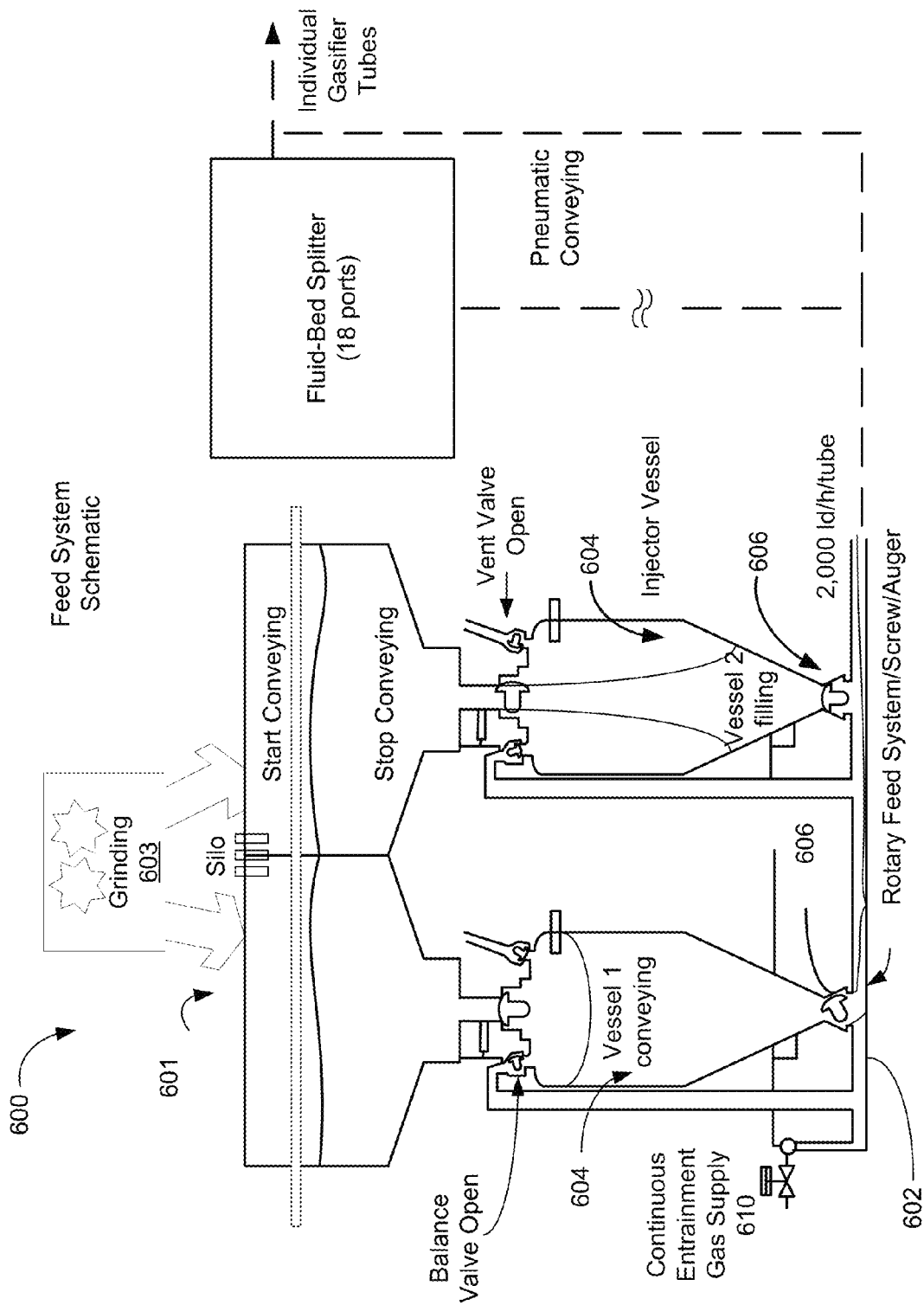

FIGS. 6a and 6b illustrate block diagrams of embodiments of the entrained-flow biomass feed system 600. Different types of feed systems may be used in conjunction with a biomass reactor, for example, drop tube, total solid feed into the reactor, slurry feed into the reactor, a moveable bed in the reactor, or combinations of these schemes. One or more feeding vessels in the biomass feed system supply two or more reactor tubes in the solar-driven chemical reactor. Each of the feeding vessels has one or more outlets configured to supply a consistent volumetric amount of biomass particles within 10 percent of the demand signal amount when distributing biomass particles to the two or more reactor tubes. For example, the injection rate to each injection point into carrier gas lines is within +/−10% of the desired demand signal amount. In an embodiment, each of the feeding vessels has one or more outlets configured to supply a consistent volumetric amount of biomass particles within 5 percent of the demand signal amount when distributing biomass particles to the two or more reactor tubes for a tighter controlled system. In an embodiment, each of the feeding vessels has one or more outlets configured to supply a consistent volumetric amount of biomass particles within 20 percent of the demand signal amount when distributing biomass particles to the two or more reactor tubes for a system more tolerant of particle size.

One example solar-driven bio-refinery may include the entrained-flow biomass feed system 600 that includes or otherwise cooperates with a grinding system. The grinding process 603 and feed process may be 1) processes separated in time and completed independently of the other process or 2) a continuous process of the where the grinding process 603 occurs and immediately feeds biomass into the feed system and then into the chemical reactor.

An objective of the feeding system is to feed as many reactor tubes as possible with the fewest number of feeding vessels such as lock-hopper systems. The reactor tubes fed by a single lock-hopper system can be referred as tube subset. Therefore, the total number of the reactor tubes in the solar receiver in some embodiments may be the product of the number of lock-hopper systems and the number of tubes in the tube subset. A lock-hopper system may comprise of either a single isolating lock-vessel followed by the injection vessel or of a pair of injection vessels operating sequentially—as one discharges the other fills.

One or more combinations of the following example feeding vessels can achieve feeding multiple reactor tubes within a tube subset by a single lock-hopper system. The feeding vessel may use an Auger/Screw feeder or an airlock-type rotational solids feeding/rate metering device. A screw feeder type that controls biomass particle feeding/rate will be discussed and a RotoScrew™ will be given as a common example of this type. An airlock-type rotational metering device that controls biomass particle feeding/rate and uses entrainment gas to carry solids along the axis of rotation will be discussed and a RotoFeed™ will be given as a common example of this type.

An embodiment of the feeding vessel has the injection vessel configured to discharge ground particles of biomass through a multiplicity of single-outlet rotational feed devices, such as the screw feeder type or the airlock type, that provide a consistent volumetric federate, each feeding separate biomass entrainment lines. The rotational speed of each of the rotational feed devices is controlled independently. Each of the rotational feed devices feeds a separate reactor tube.

An embodiment of the feeding vessel has the injection vessel configured to discharge ground particles of biomass via a multi-outlet rotational device such as a (RotoFeed™). All the outlets have the same nominal biomass feed rate controlled by the rpm on the RotoFeed™.

An embodiment of the feeding vessel has the injection vessel configured to discharge ground particles of biomass via a single-outlet rotational device (RotoFeed™ or RotoScrew™) to the main pneumatic conveying line equipped with a fluid-bed splitter, which then without any moving parts evenly splits the incoming main biomass feed into a number of feed lines, each feeding a single tube of the tube subset. All the splits into the feed lines have the same nominal biomass feed rate controlled by the revolutions per minute on the RotoFeed™ or RotoScrew™.

The grinding system 603, such as a hammer mill system, KDS, etc. may have a conveyer bringing biomass potentially in bales, which are debaled via a bale cutter/debaler, and then grinds the de-baled biomass into particles via a mechanical cutting device cooperating with a set of filters with specific sized holes in the filters. The grinding system 603 generates particles that have an average smallest dimension size between 200 um and 2000 um, such to fit through the holes in the filters, with a general range of between 500 um and 1000 um. The primary particles are then loaded into a lock hopper system 601 with a standard belt or pneumatic conveyer. The lock hopper system may have one or more injection vessels. The lock hopper 604 has one or more output ports to then feed the biomass particles across a pressure boundary into the pressurized entrainment carrier gas for feeding one or more feed lines into in the solar-driven chemical reactor.

In some embodiments, the grinding equipment 603, for example, hammer mills and flail mills provide biomass material reliably in the entire particle size range of interest for solar gasifier. The grinding system 603 may be equipped with a classifier such as a series perforated screens followed by a cyclone at the outlet, in order to control the outlet particle size of the biomass to be between 50 um and 2000 um, with a general range of 500 um to 1000 um. Thus, the morphology of the biomass in conjunction with the specifics of the grinding equipment can be controlled for reaching a certain biomass particle size. For example, in some systems, the re-ground particles having an average size between 50 um and 2000 um are then loaded into the lock hopper system with a standard belt conveyer.

As illustrated in FIGS. 6a and 6b, the entrained-flow biomass feed system 600 can include a pressurized lock hopper 604 that feeds the biomass to a rotating metering feed screw 602 and then into an entrainment gas pipe at the lock hopper exit 606. The particles of the biomass are distributed into multiple entrainment gas lines by a flow splitter to feed the two or more reactor tubes making up the solar-driven chemical reactor.

One or more methanol units may be in the on-site fuel synthesis reactor. The gas source 610 may supply a hydrocarbon gas, pressurized dry steam, or other gas as the entrainment carrier gas for the entrained-flow biomass feed system. Note, the pressurized dry steam can be generated from waste heat recovered from at least one of 1) the hydrocarbon fuel synthesis process in the on-site fuel synthesis units and 2) the reaction products from the gasification reaction coming out of the solar-driven chemical reactor.

The solar-driven bio-refinery may also include the entrained-flow biomass feed system 600 having a lock-hopper equipped with a single multi-outlet RotoFeed™ that simultaneously feeds the particles of the biomass into one or more pressurized entrainment gas lines that feed the solar-driven chemical reactor. The gas source 610 may also supply pressurized entrainment gas in the form of recycled carbon dioxide from an amine acid gas removal step in the hydrocarbon fuel synthesis process. The multi-outlet RotoFeed™ provides and controls an amount of distribution of the particles of the biomass to the one or more pressurized entrainment gas lines that feed the two or more reactor tubes in the solar-driven chemical reactor.

In some embodiments, the entrained-flow biomass feed system 600 includes a lock-hopper equipped with a single multi-outlet RotoFeed™ pneumatic splitter system. The multi-outlet RotoFeed™ is configured to simultaneously split biomass feed among up to twelve feed gas entrainment lines from a single lock hopper.

The entrained-flow biomass feed system 600 can include a multi-outlet lock hopper with a number of metering rotating screws to feed each of the separate feed lines. The feed rate is controlled by each feed line's metering screw and controlling the rotational rate of the screw at the base of the lock hopper, which responds to a feed demand signal from a computerized control system, and the computerized control system controls a flow rate of particles of biomass in the solar-driven chemical reactor based on an amount of solar energy available indicated by sensors for the chemical reactor including temperature sensors and/or light meters.

High pressure feeding of solids of biomass with gasification at pressure may reduce capital cost due to the ability to use smaller compressors in the post-gasification MTG or GTL processes. Additionally, operating cost may be reduced because energy for pressurizing carrier gas comes from the sun, as opposed to from electricity. The lock hopper system can feed the reactor processes at pressure. For example, the feeding system can entrain the biomass materials in steam at high pressure, successfully disengage the particulates in the cyclone system, and distribute flow appropriately to the reactor tubes. Alternatively, the high-pressure entrainment gas can be used in the form of natural gas that is supplied at elevated pressure in which case the methane component of the entrainment gas may be reformed with the steam to provide additional amounts of carbon monoxide and hydrogen. Moreover, because of the methane being reformed with steam simultaneously with biomass gasification the methane to biomass feed ratio can be used as means of controlling the quality of the product syngas.

The computer control system may determine the temperatures, and control the residence times and the amount of particles traveling through the downdraft reactor at a particular time to achieve high conversion, and may lead to almost complete gasification of the biomass, including lignin fractions. Due to intrinsic variability in the available solar energy, the biomass feed rate for a given amount of concentrated solar energy from the concentrating field needs to be controlled by the computer control system to adjust biomass in verses the heat sink effect in the solar receiver and reactor of the biomass in the reactor tubes using the heat of the receiver and reactor to drive the gasification reaction; and thus, a balancing of mass in to supplied energy occurs to keep the target set point reactor tube temperature in a controlled temperature range. In some embodiments, the computer control system may use computational models incorporating full mass and energy balances to predict the temperature history of the flowing particles and solar energy distribution within the receiver cavity for reaction rate. In some systems, the biomass particles can be fed to a multi-tube downdraft solar thermal receiver/reactor, in which the biomass is gasified in the presence of steam at temperatures exceeding 950-1000° C. For example, in some systems, the biomass can be gasified at 1000° C., 1150° C., 1200° C., and 1300° C. with residence times ranged between 0.01 s and 5.0 s.

The computer control system may send signals to the feeding vessel's metering device and/or rotational device to have all of the reactor tubes in a tube subset active and then turn up/down feed rate in all of the reactor tubes in the chemical reactor simultaneously. The biomass feed rate within each of the tubes may still vary within a wide range (for example, 5:1). Note, if the entrainment gas requirements to feed each tube are independent of the biomass rate, the product quality (composition) may vary with the biomass feed rate (dilution by the entrainment gas effect). The metering devices have been designed to have a potentially high turn-down ratio.

The computer control system may send signals to the feeding vessel's metering device and/or rotational device to have some of the reactor tubes in a tube subset active and some having biomass particle flow turned off. The chemical reactor has the reactor tubes operating at a nominal (or at least within a narrow biomass feed rate range) and the signal to the feed vessel varies the number of the tube-subsets participating in the gasification reaction. The turn-down ratio set by the number of tube subsets and the number of tubes per subsets is easier to control. Also, the uniform quality of the produced reaction products is also relatively independent of the amount of biomass supplied to the chemical reactor.

The heat from the gasification reaction products can be put to useful work. The system can also use a counter flow heat exchange to heat the carrier gas up to a temperature below 300° C. and keeping the temperature below 300° C. By using heat exchangers the system may recuperate waste heat from other process areas, which can decrease the amount of concentrated light needed to rapidly heat the biomass to a tar free temperature zone and the need for a secondary concentrator.

Figure 7:
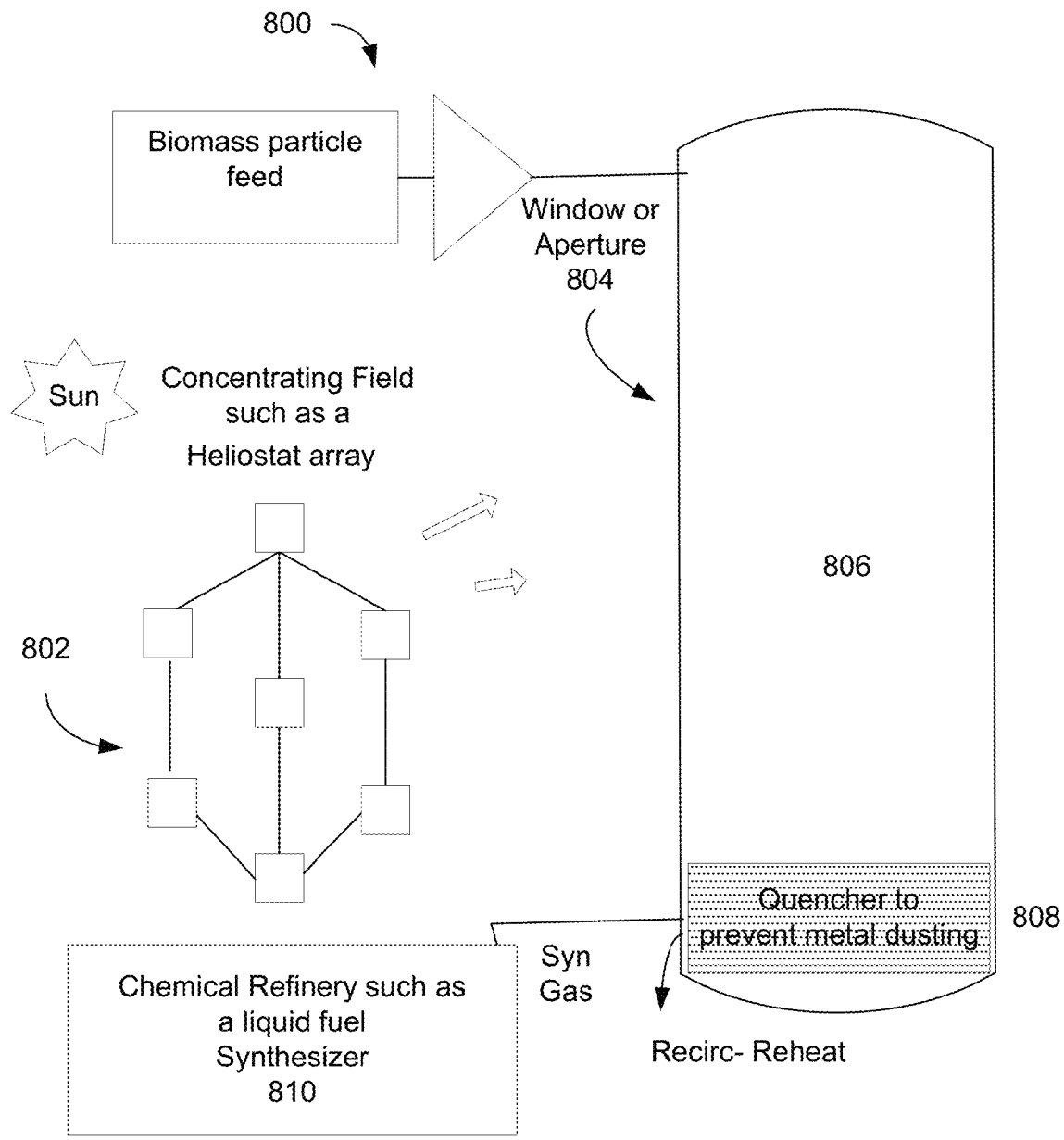
FIG. 7 illustrates a diagram of an embodiment of a solar-driven bio-refinery.

FIG. 7 illustrates a diagram of an embodiment of a solar-driven bio-refinery 800. In such a system, solar power 802 may be provided through a window or aperture 804 to a solar heated reactor chamber 806. A quencher 808 may be used to prevent back reaction. As illustrated, biomass particles flow into the system at 810 and syngas flows out 812. Additionally, a heat exchange may occur between the biomass particles and the syngas.

For example, some embodiments may include a torrefaction unit that is geographically located on the same site as the solar-driven chemical reactor. The torrefaction unit subjects the biomass to partial pyrolysis with recouped waste heat in a temperature range of 100-300° C. to make the biomass 1) brittle and easier to grind, 2) dryer, less sticky, and easier to feed in conveying system, 3) subject to less spoilage issues in storage as a torrefied biomass. The off gases from the torrefaction process can be used for an entrainment carrier gas, or can be processed to generate steam and/or electricity. The torrefaction unit supplies the partially pyrolyzed biomass to the grinding system which requires less energy to grind partially pyrolyzed biomass to the controlled particle screen size between 500 um and 1000 um.

For example, in some embodiments, an on-site fuel synthesis reactor 808 may receive the hydrogen and carbon monoxide products from the gasification reaction and use the hydrogen and carbon monoxide products in a hydrocarbon fuel synthesis process to create a liquid hydrocarbon fuel. The fuel synthesis reactor 806 may be geographically located on the same site as the chemical reactor and integrated into the process to utilize the hydrogen and carbon monoxide products from the gasification reaction.

In an example solar-driven bio-refinery, a 2-phase control system can also include a pinch valve system on each feed line to each reactor tube that receives dynamic feedback from the computerized control system to control an amount of compression of a flexible pipe section of the feed line that the biomass particles are flowing through. The entrained-flow biomass feed system can use an entrainment carrier gas and supplies biomass as particles into each of the reactor tubes of the solar-driven chemical reactor. For example, a separate entrainment line and metering device of the entrained-flow biomass feed system is used for each of the gasifier reactor tubes in the chemical reactor. This can allow balancing of 1) an amount of the particles of non-food biomass flowing to each reactor tube to 2) a temperature of that reactor tube in the multiple tube solar-driven chemical reactor. The concentrated solar thermal energy drives gasification of the biomass at an exit temperature that may exceed 950 degrees ° C. to achieve a greater than 90% conversion of biomass particles to at least hydrogen and carbon monoxide products with low to zero tar production from the gasification reaction in some embodiments.

As discussed above, the entrained-flow biomass feed system supplies a variety of three or more types of biomass that can be fed, individually or in combinational mixtures of biomass sources fed as particles into the solar-driven chemical reactor as long as a few parameters are controlled, including particle size of the biomass supplied by the feed lines, without having to change the components making up the feed system. In some embodiments, a solar-driven bio-refinery allows for feedstock flexibility in the type of biomass making up the particles of biomass because the design also obviates any need for an exothermic/endothermic reaction balancing in the chemical reactor. The concentrated solar energy drives the endothermic gasification reaction and thereby the biomass need not be burned. Thus, at least two or more different types of biomass materials might be used in the same reactor tube geometry in some example systems. This can obviate any need for a complete reengineering when a new type of biomass feedstock is used. It will be understood that multiple feed stocks could be used simultaneously or one feedstock might be used at a time.

Some systems may use commercially available grades of fumed silica blended with the biomass to aid in a bulk flow of the biomass materials that otherwise would tend to bridge due to strong Van der Waals inter-particle forces. This assists in the three or more types of biomass that can be fed, individually or in combinational mixtures without having to change the components making up the feed system. Factors causing the presence of these forces include moisture and "sticky" organics (such are resins typically found in woody biomass materials). Some systems may use Aerosil™ and Spernat™ from the product line, which is a product of Evonik Industries AG. A mechanical agitator in the lock hopper or feeding vessel can also be used to enhance the bulk flow of biomass particles that might otherwise tend to bridge in the vessel due to Van der Waal's forces.

Example systems may use an addition of 1-15% (1-2% more likely) of a bulk flow aid (silica) to our biomass raw materials in order to mitigate adverse effects of variable moisture levels and difference in chemical composition of our biomass raw materials, thereby increasing the operability of our plants in spite of the wide range of raw biomass materials considered.

Some embodiments may use the waste ash produced by the solar gasifier. An ash source may be in the entrained-flow biomass feed system to add the waste ash to the raw biomass particles. The added waste ash aids in a bulk flow of the combined materials that otherwise would tend to bridge due to strong Van der Waals inter-particle forces. This assists in the three or more types of biomass that can be fed, individually or in combinational mixtures without having to change the components making up the feed system. The feed lines carry the biomass particles with the waste ash. In this way, the waste ash can be recycled. In some embodiments, it may resemble or even exceed the performance of commercially available fumed silica. Additionally, in some embodiments, the bulk flow aid could be added to the biomass during the pulverizing (grinding) step or in a post-pulverizer blender.

Figure 8:
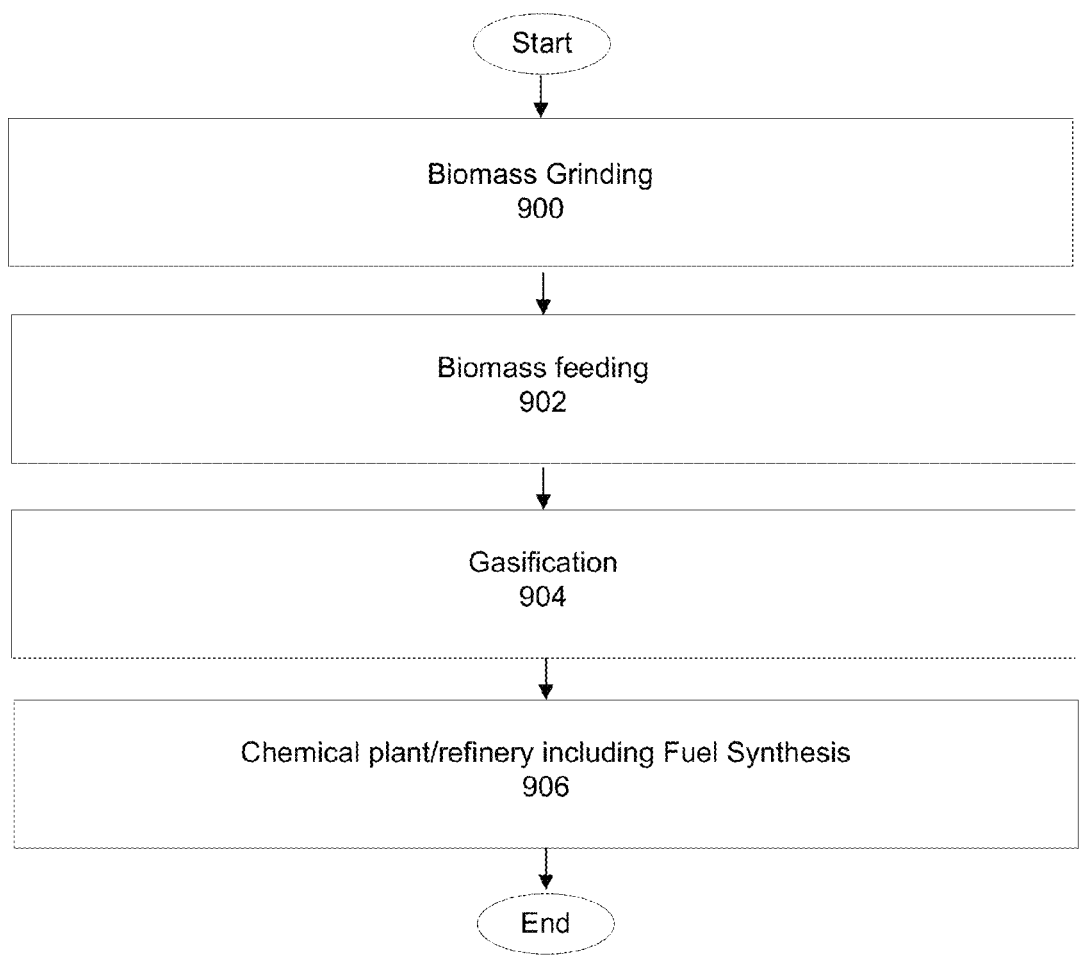
FIG. 8 illustrates a flow diagram of an embodiment of the system.

FIG. 8 illustrates a flow diagram of an embodiment of the system. In step 900, biomass grinding can occur. Equipment generally used for grinding biomass includes impact mills (e.g. hammer mills), attrition mills, and kinetic disintegration mills (e.g. flail mills). A hammer mill system can be used to grind the biomass into primary particles, which are to be fed into the solar thermal gasifier. The ground particles have an average screen size between 500 um and 1000 um, and are loaded into the lock hopper system with a standard belt or pneumatic conveyer.

In step 902 biomass feeding occurs. In some embodiments, high pressure feeding may be used. High pressure feeding of solids of biomass with gasification at pressure may reduce capital cost of the downstream liquid fuel plant 906 due to the ability to use smaller compressors in some such systems. Additionally, operating cost may be reduced because energy for pressurizing carrier gas comes from the sun, as opposed to from electricity. The lock hopper system can feed the reactor processes at pressure.

In step 904 gasification occurs. For example, in some embodiments, concentrated solar thermal energy drives gasification of the particles of the biomass to generate at least hydrogen and carbon monoxide products from the gasification reaction. In contrast to commercial chemical reactors, this chemical reactor design may have a cyclic operation rather than a continuous steady state operation. This design and its operational strategy are designed with the goal of cyclic operation, such as diurnal operation.

In step 906 fuel synthesis occurs. An on-site fuel synthesis reactor can receive the hydrogen and carbon monoxide products from the gasification reaction and use the hydrogen and carbon monoxide products in a hydrocarbon fuel synthesis process to create a liquid hydrocarbon fuel. The fuel synthesis reactor may be geographically located on the same site as the chemical reactor and integrated into the process to utilize the hydrogen and carbon monoxide products from the gasification reaction.

The methods and apparatuses of the invention in some cases may be implemented using computer software. If written in a programming language conforming to a recognized standard, sequences of instructions designed to implement the methods can be compiled for execution on a variety of hardware platforms and for interface to a variety of operating systems. It will be appreciated that a variety of programming languages may be used to implement the teachings of the invention as described herein. Furthermore, it is common in the art to speak of software, in one form or another (e.g., program, procedure, application, driver,), as taking an action or causing a result. Such expressions are merely a shorthand way of saying that execution of the software by a computer causes the processor of the computer to perform an action or produce a result.

A machine-readable medium to store instructions and data of the software is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices, etc.

While some specific embodiments of the invention have been shown the invention is not to be limited to these embodiments. The invention is to be understood as not limited by the specific embodiments described herein, but only by scope of the appended claims.

We claim:

1. A bio-refinery to generate fuel product with an entrained-flow biomass feed system, comprising:
   a boiler to produce steam and to supply the steam to a steam input;
   a chemical reactor having the steam input, reactor tubes, and an exit of a gasification reaction zone, where in the chemical reactor particles of biomass are configured to be gasified in a presence of the steam from the steam input at a temperature exceeding 950 degrees C. from the exit of the gasification reaction zone of the reactor tubes of the chemical reactor to generate at least hydrogen and carbon monoxide products from a gasification reaction;
   the entrained-flow biomass feed system having two or more feed lines to supply the particles of biomass into the chemical reactor, where a gas source for a pressurized entrainment carrier gas is coupled to the entrained-flow biomass feed system, and where types of biomass that can be fed, individually or in combinational mixtures include, forestry thinnings and forestry wastes as long as a few parameters are controlled including a particle size of the particles of biomass supplied by the feed lines without having to change the components making up the feed system, where the entrained-flow biomass feed system further includes a lock hopper system where the particles of biomass are loaded into the lock hopper system with a standard belt or pneumatic conveyer, where the lock hopper has an output, which then feeds the particles of biomass across a pressure boundary into an entraining gas flow of the pressurized entrainment carrier gas for feeding via the two or more feed lines into the chemical reactor, where an outlet of each of the feed lines is configured to control a desired dispersion pattern of the particles of biomass relative to the reactor tubes to maximize radiation absorption by the particles of biomass when injected into the chemical reactor based on a shape and width of the outlet of the feed line pipe carrying the particles of biomass;
   a particle reduction system configured to receive biomass in non-particle form and to create the particles of biomass, which have dimensions of less than 2000 microns in diameter for the entrained-flow biomass feed system; and thus, to control the particle size of the particles of biomass supplied to the two or more feed lines;
   a torrefaction unit to apply heat to the particles of biomass in order to provide dried particles of biomass to enter the entrained-flow biomass feed system, in which the two or more feed lines to supply the particles of biomass; and
   a fuel synthesis reactor of the bio-refinery that is geographically located on a same site as the chemical reactor, the particle reduction system, the torrefaction unit, and the entrained-flow biomass feed system, where the fuel synthesis reactor has an input to receive the hydrogen and carbon monoxide products derived from the gasification reaction and is configured to use the hydrogen and carbon monoxide products in a hydrocarbon fuel synthesis process to create a hydrocarbon fuel product at an output of the fuel synthesis reactor.

2. The bio-refinery of claim 1, further comprising:
   a second on-site fuel synthesis reactor having an input to receive a chemical feedstock derived from the hydrogen and carbon monoxide products from the gasification reaction and configured to use the chemical feedstock in a hydrocarbon fuel synthesis process to create a liquid hydrocarbon fuel, where the second on-site fuel synthesis reactor is also geographically located on the same site as the chemical reactor and integrated into the process to utilize the hydrogen and carbon monoxide products from the gasification reaction;
   where the particle reduction system is configured to couple to the entrained-flow biomass feed system, which further includes a conveyer to bring the biomass in non-particle form to the particle reduction system that reduces a size of the particles of biomass, where the particle reduction system generates particles that have an average smallest dimension size between 200 microns (um) and 2000 um in diameter, and then the particles are loaded into a lock hopper system with a standard belt or pneumatic conveyer, where the lock hopper has an output, which then feeds the particles of biomass across a pressure boundary into the entraining gas flow of pressurized entrainment carrier gas for feeding via the two or more feed lines into the chemical reactor; and wherein the feeding vessel is a pressurized lock hopper having an injection vessel configured to discharge the particles of biomass via a single-outlet and rotational screw and then into an entrainment gas pipe, wherein the particles of biomass are distributed in the entrainment gas line by a flow splitter to feed into a number of feed lines, which each feeds its own reactor tube making up the chemical reactor.

3. The bio-refinery of claim 1, further comprising:

two or more multiple outlet lock hoppers in the lock hopper system, each multi-outlet lock hopper feeding the particles of biomass at a consistent volumetric amount of the particles of biomass into a reactor tube subset via one or more pressurized entrainment lines that feed the chemical reactor, where a first multiple outlet lock hopper is the feeding vessel and each additional multiple outlet lock hopper is another feeding vessel; and two or more reactor tubes in the chemical reactor, where each multi-outlet lock hopper provides and controls an amount of distribution of the particles of biomass to the one or more pressurized entrainment lines that feed two or more reactor tubes within a tube subset in the chemical reactor.

4. The bio-refinery of claim 1, further comprising:

two or more gasifier reactor tubes in the chemical reactor and a separate biomass entrainment/feed rate metering line is used for each of the gasifier reactor tubes in the chemical reactor, which allows independent temperature control and balancing of an amount of particles of non-food biomass flowing in each of the gasifier reactor tubes in the multiple tube chemical reactor;

wherein the feeding vessel is a lock hopper rotary feed system having an output to distribute the particles of biomass to the gasifier reactor tubes, which allows for balanced feeding to individual gasifier reactor tubes;

a screw in the lock hopper rotary feed system, wherein feed rate of the particles of biomass is controlled by a weight measuring metering device and by controlling a rotational rate of the screw that moves set amounts of biomass along the axis of rotation, and wherein the screw is located at the base of the lock hopper; and a computerized control system to send a feed demand signal to the screw and weight measuring metering device to control the feed rate of the particles of biomass in the individual gasifier reactor tubes in the chemical reactor.

5. The bio-refinery of claim 1, wherein a multiple output port lock hopper with a multiple rotational feed splitter system is configured to simultaneously feed up to twelve feed gas entrainment lines from a single lock hopper into the chemical reactor with the added ability to accurately control feed rate of the particles of biomass with a rotational rate of each rotational feed splitter.

6. The bio-refinery of claim 1, wherein the torrefaction unit is configured to subject the biomass to partial pyrolysis with recouped waste heat in a temperature of at least 100 degrees C. to make the biomass dryer, less sticky, and easier to feed in a conveying system.

7. The bio-refinery of claim 1, further comprising:

where a feeding vessel in the entrained-flow biomass feed system is configured to discharge the particles of biomass through a multiplicity of single-outlet rotational feed devices that provide a consistent volumetric feed rate, where each rotational feed device feeds a separate gas entrainment line, and where the rotational speed of each of the rotational feed devices is controlled independently, and each of the rotational feed devices feeds a separate reactor tube; and an ash source in the entrained-flow biomass feed system, where the ash source adds waste ash to the particles of biomass to aid in a bulk flow of the combined materials that otherwise would tend to bridge due to strong Van der Waals inter-particle forces and assists in three or more types of biomass that can be fed, individually or in combinational mixtures without having to change the components making up the feed system, and wherein the feed lines carry the biomass particles with the waste ash, and an outlet of each of the feed lines controls a dispersion pattern of the particles of biomass into its corresponding reactor tube to maximize radiation absorption by the particles when injected into the reactor tube based on a shape and width of the outlet of the feed line pipe carrying the particles of biomass to its corresponding reactor tube.

8. The bio-refinery of claim 1, further comprising:

wherein the lock hopper system has an airlock type of feeding rate metering device and varies an amount of biomass being supplied to the reactor tubes based on an amount of available heat to the chemical reactor and a supplied amount of biomass in order to generate the at least hydrogen and carbon monoxide products from the gasification reaction at a greater than 90% conversion rate of the biomass in a residence time.

9. The bio-refinery of claim 1, further comprising:

two or more reactor tubes in the chemical reactor;

a first sensor to indicate an amount of heat energy available;

a computerized control system configured to receive a feedback signal from a set of sensors, including the first sensor; and wherein the computerized control system controls the feed rate of the particles of biomass material into the two or more reactor tubes with well controlled feed rates based on two factors of 1) amount of biomass material and 2) amount of heat available given as feedback to the computerized control system by the first sensor.

10. The bio-refinery of claim 1, wherein the chemical reactor has multiple reaction tubes in a downdraft orientation, and the feed system feeds the biomass particles into the multiple reaction tubes, in which the particles of biomass are gasified in the presence of steam at the temperature exceeding 950 degrees C. from the exit of the gasification reaction zone of the reactor tubes to generate the at least hydrogen and carbon monoxide products from the gasification reaction, and wherein a computerized control system is configured to send a signal to vary an amount of the reactor tube subsets participating in the gasification reaction by turning on or turning off a flow of the particles of biomass from the feed vessel to one or more reactor tubes in the tube subset.

11. The bio-refinery of claim 9, further comprising:

one or more temperature sensors in the chemical reactor; and where the computerized control system in the entrained-flow biomass feed system is further configured to control a biomass flow rate for the particle size and type of biomass and current temperature in each reactor tube required to achieve from the gasification reaction a greater than 90 percent conversion of the particles of biomass into the at least hydrogen and carbon monoxide products with low tar production of less than 50 milligrams per normal cubic meter.

12. The bio-refinery of claim 1, wherein the particles of biomass are pneumatically fed from the entrained-flow biomass feed system via the entrainment carrier gas to the chemical reactor, and the particles of biomass are pre-heated prior to entry into the chemical reactor by the entrainment carrier gas, where the entrainment carrier gas is at least one of carbon dioxide gas and steam, which is heated by waste heat from the reaction products of the gasification reaction coming out of the chemical reactor by a counter flow heat exchanger using the waste heat as its heat source to heat the entrainment carrier gas up to a maximum temperature of 300 degrees C.

13. The bio-refinery of claim 1, further comprising:
a computerized control system configured to balance the amount of biomass particles flowing in each of the reactor tubes and the amount of heat energy available.

14. The bio-refinery of claim 13, wherein the 2-phase control system is a pinch system on each feed line to each reactor tube that receives dynamic feedback from the computerized control system to control an amount of compression of a flexible pipe section of the feed line that the particles of biomass are flowing through; and
wherein a filtered form of the carbon monoxide and hydrogen resulting from the chemical reaction in the chemical reactor is supplied to the input of the downstream fuel synthesis reactor, in which methanol is generated from the fuel synthesis reactor, and then supplied to a Methanol-to-Gasoline process.

15. The bio-refinery of claim 2, further comprising:
a flow enhancer, including a bulk flow enhancer or a porous-walled tube, in the entrained-flow biomass feed system to control an amount of entrainment carrier gas carrying the particles of biomass entering the gasification reaction zone of the reactor tubes by reducing velocity of the carrier gas just prior to an entrance to a gasification reaction zone of the reactor tubes by removing a controlled portion of the carrier gas through the flow enhancer in response to a feedback signal; and
a computerized control system in the entrained-flow biomass feed system configured to balance the amount of biomass particles flowing in each of the reactor tubes based on an amount of heat energy available by controlling the resistance to flow in each tube via the addition or removal of carrier gas through the flow enhancer.

16. The bio-refinery of claim 1, wherein the chemical reactor is a multiple reactor tube, downdraft, chemical reactor, and the entrained-flow biomass feed system carries biomass as particles into each of the reactor tubes of the chemical reactor, the entrained-flow biomass feed system further comprising:
a feeding vessel that supplies a tube subset of two or more reactor tubes in the chemical reactor, where the feeding vessel has one or more outlets configured to supply a consistent volumetric amount of biomass particles within 10 percent of the demand signal amount when distributing biomass particles to the two or more reactor tubes; and
a separate entrainment line and metering device used for each of the gasifier reactor tubes in the chemical reactor, which allows balancing of 1) an amount of the particles of non-food biomass flowing to each reactor tube to 2) a temperature of that reactor tube in the multiple tube chemical reactor, wherein the thermal energy drives gasification of the biomass at an exit temperature exceeding 950 degrees C. to achieve from the gasification reaction a greater than 90% conversion of the particles of biomass to at least hydrogen and carbon monoxide products with low tar production of less than 50 mg/Nm$^3$.

17. The bio-refinery of claim 16, further comprising:
an on-site fuel synthesis reactor having an input configured to receive the hydrogen and carbon monoxide products from the gasification reaction and configured to use the hydrogen and carbon monoxide products in a hydrocarbon fuel synthesis process to create a liquid hydrocarbon fuel,
wherein the entrained-flow biomass feed system includes a common entrainment line, a multiple port lock hopper with a metering device and a rotating screw to feed each of the separate feed lines,
where feed rate is controlled by each feed line's metering device and controlling the rotational rate of the screw at the base of the lock hopper, which responds to a feed demand signal from a computerized control system.

18. The bio-refinery of claim 16, wherein the entrained-flow biomass feed system further comprises an ash source to add waste ash to the biomass to aid in a bulk flow of the combined materials that otherwise would tend to bridge due to strong Van der Waals inter-particle forces.

19. The bio-refinery of claim 16, wherein the chemical reactor is a chemical reactor aligned to receive concentrated solar thermal energy from one or more solar energy concentrating fields including an array of heliostats, solar concentrating dishes or any combination of these two, and
balancing the amount of biomass particles flowing into each of the reactor tubes to an amount of solar energy available is accomplished via a control system to control flow in the individual reactor tubes by controlling a rotational rate of a screw of a lock hopper feeding the biomass where all the tubes in the tube subset have their feed rate simultaneously turned up or turned down, and wherein the entrained-flow biomass feed system further comprises a silica source to add silica to the particles of biomass to aid in a bulk flow of the combined materials that otherwise would tend to bridge due to strong Van der Waals inter-particle forces and assists in the three or more types of biomass that can be fed, individually or in combinational mixtures without having to change the components making up the feed system, wherein the silica comprises fumed silica, the silica comprises 1-15% of the bulk flow, and the bulk flow aid is added to the biomass during pulverization, and wherein the silica comprises 2-5% of the bulk flow, and the bulk flow aid is added to the biomass during pulverization.

* * * * *